US008449470B2

(12) United States Patent
Blanco et al.

(10) Patent No.: US 8,449,470 B2
(45) Date of Patent: May 28, 2013

(54) SYSTEM FOR REPETITIVE MEASUREMENTS OF CARDIAC OUTPUT IN FREELY MOVING INDIVIDUALS

(75) Inventors: Cesar Blanco, Los Angeles, CA (US); Frances Richmond, South Pasadena, CA (US); Daniel P. Holschneider, Los Angeles, CA (US); Jean-Michel I. Maarek, Rancho Palos Verdes, CA (US)

(73) Assignee: Alfred E. Mann Institute for Biomedical Engineering at the University of Southern California, Los Angeles, CA (US)

( * ) Notice: Subject to any disclaimer, the term of this patent is extended or adjusted under 35 U.S.C. 154(b) by 951 days.

(21) Appl. No.: 12/544,957

(22) Filed: Aug. 20, 2009

(65) Prior Publication Data

US 2010/0042007 A1 Feb. 18, 2010

Related U.S. Application Data

(60) Division of application No. 11/774,229, filed on Jul. 6, 2007, now abandoned, which is a continuation-in-part of application No. 10/847,480, filed on May 17, 2004, now Pat. No. 7,590,437, which is a continuation of application No. 10/153,387, filed on May 21, 2002, now Pat. No. 6,757,554.

(51) Int. Cl.
*A61B 5/02* (2006.01)
*A61B 6/00* (2006.01)

(52) U.S. Cl.
USPC ............ 600/483; 600/504; 600/479; 600/526

(58) Field of Classification Search
USPC ................. 600/481, 483, 484, 504–508, 513, 600/526
See application file for complete search history.

(56) References Cited

U.S. PATENT DOCUMENTS

| | | | |
|---|---|---|---|
| 4,109,647 A | 8/1978 | Stern et al. |
| 4,303,336 A | 12/1981 | Cullis |
| 4,326,539 A | 4/1982 | Obermajer |
| 4,730,622 A | 3/1988 | Cohen |
| 5,217,456 A | 6/1993 | Narciso, Jr. |
| 5,331,958 A | 7/1994 | Oppenheimer |
| 5,685,989 A | 11/1997 | Krivitski et al. |
| 5,687,726 A | 11/1997 | Hoeft |
| 5,697,371 A | 12/1997 | Aoyagi et al. |
| 5,766,125 A | 6/1998 | Aoyagi et al. |
| 5,797,396 A | 8/1998 | Geiser et al. |
| 5,830,365 A | 11/1998 | Schneditz |

(Continued)

FOREIGN PATENT DOCUMENTS

WO 2006039731 A1 4/2006

OTHER PUBLICATIONS

Darovic, G.O. 1995. Hemodynamic monitoring. Chapter 11: Monitoring cardiac output. pp. 327-332, 344-346. 2d Ed. W.B. Saunders.

(Continued)

*Primary Examiner* — Navin Natnithithadha
(74) *Attorney, Agent, or Firm* — McDermott Will & Emery LLP

(57) ABSTRACT

A system for evaluating the cardiovascular system parameters using indicator dilution and non-invasive or minimally invasive detection and calibration methods are disclosed. Intravascular indicators are stimulated, and emissions patterns detected for computation of cardiac output, cardiac index, blood volume and other indicators of cardiovascular health.

24 Claims, 20 Drawing Sheets

U.S. PATENT DOCUMENTS

| | | | |
|---|---|---|---|
| 5,999,841 | A | 12/1999 | Aoyagi et al. |
| 6,041,246 | A | 3/2000 | Krivitski et al. |
| 6,159,445 | A | 12/2000 | Klaveness et al. |
| 6,178,340 | B1 | 1/2001 | Svetliza |
| 6,219,566 | B1 | 4/2001 | Weersink et al. |
| 6,223,069 | B1 | 4/2001 | Pfeiffer et al. |
| 6,228,344 | B1 | 5/2001 | Dorshow et al. |
| 6,230,035 | B1 | 5/2001 | Aoyagi et al. |
| 6,280,386 | B1 | 8/2001 | Alfano et al. |
| 6,280,703 | B1 | 8/2001 | Combs et al. |
| 6,299,583 | B1 | 10/2001 | Eggers et al. |
| 6,424,857 | B1 | 7/2002 | Henrichs et al. |
| 6,493,567 | B1 | 12/2002 | Krivitski et al. |
| 6,542,769 | B2 | 4/2003 | Schwamm et al. |
| 6,554,775 | B1 | 4/2003 | Peyman et al. |
| 6,718,190 | B2 | 4/2004 | Krivitski et al. |
| 6,746,408 | B2 | 6/2004 | Krivitski et al. |
| 6,746,415 | B1 | 6/2004 | Steuer et al. |
| 6,986,744 | B1 | 1/2006 | Krivitski |
| 7,261,696 | B2 | 8/2007 | Krivitski |
| 2002/0151774 | A1 | 10/2002 | Soller et al. |
| 2003/0060722 | A1 | 3/2003 | Pfeiffer et al. |
| 2004/0156782 | A1 | 8/2004 | Alam et al. |
| 2005/0020891 | A1 | 1/2005 | Rubinstein et al. |

OTHER PUBLICATIONS

Desmettre, T. et al. 2000. Fluorescence properties and metabolic features of indocyanine green (ICG) as related to angiography. Survey of opthalmology. Jul.-Aug. 2000. vol. 45, No. 1, pp. 15-27.

Diamond, K.R. et al. 2003. Quantification of fluorophore concentration in tissue-simulating media by fluorescence measurements with a single optical fiber. Applied Optics, May 1, 2003, vol. 42, No. 13, pp. 2436-2442.

Dorshow. R.B. et al. 1998. Noninvasive fluorescence detection of hepatic and renal function. Journal of biomedical optics. Jul. 1998. vol. 3, No. 3, pp. 340-345.

Edwards, A.D. et al. 1993. Measurement of hemoglobin flow and blood flow by near-infrared spectroscopy. J. Applied Physiology, vol. 75, pp. 1884-1889.

Fok. T.-F. et al. 2001. Oxygen consumption by lungs with acute and chronic injury in a rabbit model. Intensive care medicine. vol. 27, pp. 1532-1538.

Geddes, L.A. 1984. Cardiovascular devices and their applications. Chapter 4: The measurement of cardiac output and blood flow. pp. 101-122, 186-188. John Wiley & Sons, New York.

Hollins, B. et al. 1987. Fluorometric determination of indocyanine green in plasma. Clinical chemistry. pp. 765-768. vol. 33, No. 6.

Iijima T. et al. 1997. Cardiac output and circulating blood volume analysis by pulse dye densitometry. Journal of Clinical Monitoring, vol. 13, pp. 81-89.

International Search Report for PCT Application No. PCT/US2007/015650, filed Jul. 9, 2007, mailed Aug. 20, 2008.

Nihon Kohden. 2001. website: http://kohden.co.jp/intl/ppms-ddg2001.html. Website viewed May 17, 2001.

Preckel, B. et al. 2000. Effect of dantrolene in an in vivo and in vitro model of myocardial reperfusion injury. Acta Anaesthesiol Scand. vol. 44, pp. 194-201.

Sakka, G. et al. 2002. Comparison of Cardiac Output and Circulatory Blood volumes by Transpulmonary Thermo-dye Dilution and Transcutaneous Indocyanine Green Measurement in Critically Ill Patients. Feb. 2002. CHEST, vol. 121, No. 2, pp. 559-565.

Wang, L. et al. 1995. MCML—Monte Carlo modeling of light transport in multi-layered tissues. Computer Methods & Programs in Biomedicine, vol. 47, No. 2, pp. 131-146.

Weersink et al. 2001. Noninvasive measurement of fluorophore concentration in turbid media with a simple fluorescence/reflectance ratio technique. Applied Optics, Dec. 2001, vol. 40, No. 34, pp. 6389-6395.

SYSTEM FOR REPETITIVE MEASUREMENTS OF CARDIAC OUTPUT IN FREELY MOVING INDIVIDUALS

CROSS-REFERENCE TO RELATED APPLICATIONS

This application is a divisional application of U.S. patent application Ser. No. 11/774,229, filed Jul. 6, 2007 now abandoned, entitled "System for Repetitive Measurements of Cardiac Output in Freely Moving Individuals"; which is a continuation-in-part of U.S. patent application Ser. No. 10/847,480, now U.S. Pat. No. 7,590,437 filed May 17, 2004, entitled "Measurement of Cardiac Output and Blood Volume by Non-Invasive Detection of Indicator Dilution"; which is Continuation of U.S. patent application Ser. No. 10/153,387, filed May 21, 2002 (now U.S. Pat. No. 6,757,554, issued Jun. 29, 2004) entitled "Measurement of Cardiac Output and Blood Volume by Non-Invasive Detection of Indicator Dilution." This application also relates to U.S. patent application Ser. No. 11/625,184, filed Jan. 19, 2007, entitled "Method and Apparatus for Measurement of Cardiac Output and Blood Volume by Non-Invasive Detection of Indicator Dilution"; U.S. patent application Ser. No. 11/744,147, filed May 3, 2007 (now U.S. Pat. No. 7,474,906), entitled "Method for Dye Injection for the Transcutaneous Measurement of Cardiac Output"; and U.S. patent application Ser. No. 11/744,157, filed May 3, 2007, entitled "Method and Apparatus for Measurement of Cardiac Output and Blood Volume By Non-invasive Detection of Indicator Dilution for Hemodialysis." The content of all of these applications is incorporated herein by reference.

FIELD OF THE INVENTION

This invention pertains to the detection of parameters of cardiovascular system of a subject.

GENERAL BACKGROUND AND STATE OF THE ART

Cardiac output is a central part of the hemodynamic assessment in patients having heart disease, acute hemodynamic compromise or undergoing cardiac surgery, for example. Cardiac output is a measure of the heart's effectiveness at circulating blood throughout the circulatory system. Specifically, cardiac output (measured in L/min) is the volume of blood expelled by the heart per beat (stroke volume) multiplied by the heart rate. An abnormal cardiac output is at least one indicator of cardiovascular disease.

The current standard method for measuring cardiac output is the thermodilution technique (Darovic, G. O. Hemodynamic monitoring: invasive and noninvasive clinical application. 2nd Ed. W.B. Saunders, 1995). Generally, the technique involves injecting a thermal indicator (cold or heat) into the right side of the heart and detecting a change in temperature caused as the indicator flows into the pulmonary artery.

Typically, the thermodilution technique involves inserting a flow-directed balloon catheter (such as a Swan-Ganz catheter) into a central vein (basilic, internal jugular or subclavian) and guiding it through the right atrium and ventricle to the pulmonary artery. The balloon catheter is typically equipped with a thermistor near its tip for detecting changes in blood temperature. A rapid injection of a bolus of chilled glucose solution (through a port in the catheter located in the vena cava near the right atrium) results in a temperature change in the pulmonary artery detected with the thermistor. The measured temperature change is analyzed with an external electronic device to compute the cardiac output. The algorithm implemented in this computation is typically a variant of the Stewart-Hamilton technique and is based on the theory of indicator mixing in stirred flowing media (Geddes L A., Cardiovascular devices and measurements. John Wiley & Sons. 1984).

Thermodilution measurements of cardiac output are disadvantageous for several reasons. First, placement of the thermodilution balloon catheter is an expensive and invasive technique requiring a sterile surgical field. Second, the catheter left in place has severe risks to the patient such as local infections, septicemia, bleeding, embolization, catheter-induced damage of the carotid, subclavian and pulmonary arteries, catheter retention, pneumothorax, dysrrhythmias including ventricular fibrillation, perforation of the atrium or ventricle, tamponade, damage to the tricuspid values, knotting of the catheter, catheter transection and endocarditis. Third, only specially trained physicians can insert the balloon catheter for thermodilution cardiac output. Last, thermodilution measurements of the cardiac output are too invasive to be performed in small children and infants.

Another method used for measuring cardiac output is the dye indicator dilution technique. In this technique, a known volume and concentration of indicator is injected into the circulatory flow. At a downstream point, a blood sample is removed and the concentration of the indicator determined. The indicator concentration typically peaks rapidly due to first pass mixing of the indicator and then decreases rapidly as mixing proceeds in the total blood volume (~10 seconds; first pass concentration curve). Further, indicator concentration slowly diminishes as the indicator is metabolized and removed from the circulatory system by the liver and/or kidneys (time depending upon the indicator used). Thus, a concentration curve can be developed reflecting the concentration of the indicator over time. The theory of indicator dilution predicts that the area under the first pass concentration curve is inversely proportional to the cardiac output.

Historically, indicator dilution techniques have involved injecting a bolus of inert dye (such as indocyanine green) into a vein and removing blood samples to detect the concentration of dye in the blood over time. For example, blood samples are withdrawn from a peripheral artery at a constant rate with a pump. The blood samples are passed into an optical sensing cell in which the concentration of dye in the blood is measured. The measurement of dye concentration is based on changes in optical absorbance of the blood sample at several wavelengths.

Dye-dilution measurements of cardiac output have been found to be disadvantageous for several reasons. First, arterial blood withdrawal is time consuming, labor intensive and depletes the patient of valuable blood. Second, the instruments used to measure dye concentrations (densitometer) must be calibrated with samples of the patient's own blood containing known concentrations of the dye. This calibration process can be very laborious and time consuming in the context of the laboratory where several samples must be run on a daily basis. Further, technical difficulties arise in extracting the dye concentration from the optical absorbance measurements of the blood samples.

A variation on the dye-dilution technique is implemented in the Nihon Kohden pulse dye densitometer. In this technique, blood absorbance changes are detected through the skin with an optical probe using a variation of pulse oximetry principles. This variation improves on the prior technique by eliminating the necessity for repeated blood withdrawal. However, as described above, this technique remains limited by the difficulty of separating absorbance changes due to the dye concentration changes from absorbance changes due to changes in blood oxygen saturation or blood content in the volume of tissue interrogated by the optical probe. This method is also expensive in requiring large amounts of dye to create noticeable changes in absorbance and a light source producing two different wavelengths of light for measuring light absorption by the dye and hemoglobin differentially. Even so, the high background levels of absorption in the circulatory system make this technique inaccurate. Finally, where repeat measurements are desired, long intervals must ensue for the high levels of the indicator to clear from the blood stream. Thus, this technique is inconvenient for patients undergoing testing and practitioners awaiting results to begin or alter treatment.

Other approaches for measuring cardiac output exist which are not based on indicator dilution principles. These include ultrasound Doppler, ultrasound imaging, and the Fick principle applied to oxygen consumption or carbon dioxide production and electric impedance plethysmography (Darovic, supra). However, these techniques have specific limitations. For instance, the ultrasound techniques (Doppler and imaging) require assumptions on the three-dimensional shape of the imaged structures to produce cardiac output values from velocity or dimension measurements.

Blood volume measures the amount of blood present in the cardiovascular system. Blood volume is also a diagnostic measure that is relevant to assessing the health of a patient. In many situations, such as during or after surgery, traumatic accident or in disease states, it is desirable to restore a patient's blood volume to normal as quickly as possible. Blood volume has typically been measured indirectly by evaluating multiple parameters (such as blood pressure, hematocrit, etc.). However, these measures are not as accurate or reliable as direct methods of measuring blood volume.

Blood volume has been directly measured using indicator dilution techniques (Geddes, supra). Briefly, a known amount of an indicator is injected into the circulatory system. After injection, a period of time is allowed to pass such that the indicator is distributed throughout the blood, but without clearance of the indicator from the body. After the equilibration period, a blood sample is drawn which contains the indicator diluted within the blood. The blood volume can then be calculated by dividing the amount of indicator injected by the concentration of indicator in the blood sample (for a more detailed description see U.S. Pat. No. 6,299,583 incorporated by reference). However, to date, the dilution techniques for determining blood volume are disadvantageous because they are limited to infrequent measurement due to the use of indicators that clear slowly from the blood.

Thus, it would be desirable to have a non-invasive, cost effective, accurate and sensitive technique for measuring cardiovascular parameters, such as cardiac output and blood volume.

SUMMARY

The present cardiovascular measurement devices and methods assess cardiovascular parameters within the circulatory system using indicator dilution techniques. Cardiovascular parameters are any measures of the function or health of a subject's cardiovascular system.

In one aspect of the present cardiovascular measurement devices and methods, a non-invasive method for determining cardiovascular parameters is described. In particular, a non-invasive fluorescent dye indicator dilution method is used to evaluate cardiovascular parameters. The method may be minimally invasive, requiring only a single peripheral, intravenous line for indicator injection into the circulatory system of the patient. Further, a blood draw may not be required for calibration of the system. Further, cardiovascular parameters may be evaluated by measuring physiological parameters relevant to assessing the function of the heart and circulatory system. Such parameters include, but are not limited to cardiac output and blood volume.

Such minimally invasive procedures are advantageous over other methods of evaluating the cardiovascular system. First, complications and patient discomfort caused by the procedures are reduced. Second, such practical and minimally invasive procedures are within the technical ability of most doctors and nursing staff, thus, specialized training is not required. Third, these minimally invasive methods may be performed at a patient's bedside or on an outpatient basis. Finally, methods may be used on a broader patient population, including patients whose low risk factors may not justify the use of central arterial measurements of cardiovascular parameters.

In another aspect of the cardiovascular measurement devices and methods, these methods may be utilized to evaluate the cardiovascular parameters of a patient at a given moment in time, or repeatedly over a selected period of time. The dosages of indicators and other aspects of the method can be selected such that rapid, serial measurements of cardiovascular parameters may be made. These methods can be well suited to monitoring patients having cardiac insufficiency or being exposed to pharmacological intervention over time. Further, the non-invasive methods may be used to evaluate a patient's cardiovascular parameters in a basal state and when the patient is exposed to conditions which may alter some cardiovascular parameters. Such conditions may include, but are not limited to changes in physical or emotional conditions, exposure to biologically active agents or surgery. For example, embodiments of the cardiovascular measurement devices and methods can be used for cardiac output monitoring before, during, or after kidney dialysis; cardiac output monitoring under shock conditions (such as, for example, septic shock, anaphylactic shock, cardiogenic shock, neurogenic shock, hypovolemic shock); cardiac output monitoring during stress tests to better understand the heart's ability to increase blood supply to the heart and body while exercising or under other conditions requiring additional blood flow through the heart; cardiac output monitoring before, during, and after chemotherapy treatment to monitor fluid equilibrium in the body; and cardiac output measurements for athletes needing to understand how their cardiac performance to improve their athletic performance.

In another aspect of the cardiovascular measurement devices and methods, modifications of the method may be undertaken to improve the measurement of cardiovascular parameters. Such modifications may include altering the placement of a photodetector relative to the patient or increasing blood flow to the detection area of the patient's body.

In yet another aspect of the cardiovascular measurement devices and methods, the non-invasive method of assessing cardiovascular parameters utilizes detection of indicator emission, which is fluorescence, as opposed to indicator absorption. Further, indicator emission may be detected in a transmission mode and/or reflection mode such that a broader range of patient tissues may serve as detection sites for evaluating cardiovascular parameters, as compared to other methods. Measurement of indicator emission can be more accurate than measurements obtained by other methods, as indicator emission can be detected directly and independent of the absorption properties of whole blood.

In a further aspect of the cardiovascular measurement devices and methods, a system for the non-invasive or minimally invasive assessment of cardiovascular parameters is described. In particular, such a system may include an illumination source for exciting the indicator, a photodetector for sensing emission of electromagnetic radiation from the indicator and a computing system for receiving emission data, tracking data over time and calculating cardiovascular parameters using the data.

In another aspect of the cardiovascular measurement devices and methods, the methods and system described herein may be used to assess cardiovascular parameters of a variety of subjects. In some embodiments, the methodology can be modified to examine animals or animal models of cardiovascular disease, such as cardiomyopathies. The methodology of the present invention is advantageous for studying animals, such as transgenic rodents whose small size prohibits the use of current methods using invasive procedures. The present cardiovascular measurement devices and methods are also advantageous in not requiring anesthesia which can effect cardiac output measurements.

In yet another aspect of the cardiovascular measurement devices and methods, a noninvasive calibration system can be used to determine the concentration of circulating indicator dye. In some embodiments, the concentration of circulating indicator dye can be determined from the ratio of emergent fluorescent light to transmitted and/or reflected excitation light.

In another aspect of cardiovascular measurement devices and methods, a noninvasive, mobile, self-contained, stand alone system can be used to repetitively perform the cardiac output measurements in freely moving individuals. The device will be worn by the individual and it will communicate remotely with a PDA/laptop/desktop computer through a wireless dongle. This will further assist the individual to freely move about during the cardiac output measurements.

In other embodiments, the methodology can be modified for clinical application to human patients. The present cardiovascular measurement devices and methods may be used on all human subjects, including adults, juveniles, children and neonates. The present invention is especially well suited for application to children, and particularly neonates. As above, the present technique is advantageous over other methods at least in that it is not limited in application by the size constraints of the miniaturized vasculature relative to adult subjects.

DETAILED DESCRIPTION

The method and system of the present invention are for the evaluation of cardiovascular parameters of a subject using an indicator dilution technique.

Figure 9:
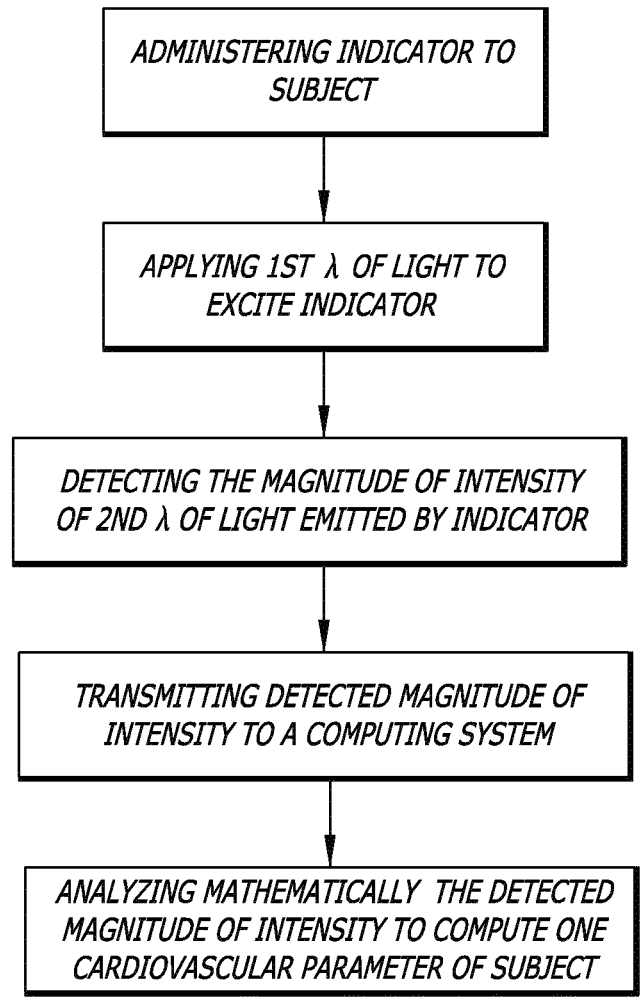
FIG. 9 is a flow chart depicting one method of the present invention.

The method of this invention generally involves the injection of a selected amount of indicator into the bloodstream of the subject (FIG. 9). Preferably, the indicator is illuminated using a first wavelength of excitation light selected to cause the indicator to fluoresce and emit a second wavelength of light. A photodetector is placed near the subject for the detection of the intensity of the emitted second wavelength of light, which is proportional to the concentration of the indicator circulating within the circulatory system. The photodetector transmits this intensity information to a computing system, which records and preferably maps the intensity curve of the indicator detected over time.

Typically, the indicator concentration values increase to a peak rapidly after injection of the indicator. Then, the concentration values decrease rapidly, then more steadily as the indicator is mixed throughout the body circulatory system and metabolized over time. A microprocessor driven computation then can calculate from the concentration curve, the patient's cardiac output and/or blood volume values. Additionally, values can be generalized repeatedly using this method, at intervals of about every 2-5 minutes.

Indicators.

The indicators useful in this invention are preferably inert and biocompatible in that they do not alter cardiovascular parameters, such as heart rate. Further, the indicator is preferably a substance that once injected, does not diffuse out of the vasculature of the cardiovascular system. Also, the indicator is preferably selected to be one which is metabolized within the body at a rate such that repeated measures using this method may be conducted at intervals of about 2-5 minutes. It is also desirable that the background levels of circulating indicator be cleared between intervals, although measurements may be taken when background levels are not zero. Finally, the indicator can be selected to be detectable by the photodetector system selected.

In one embodiment, a non-invasive dye indicator dilution method may be used to evaluate cardiovascular function. Many different dye indicators may be used within the scope of this invention. Preferably, the dye indicator is fluorescent having an excitation wavelength and an emission wavelength in the near infrared spectrum, preferably about 750 nm to about 1000 nm, and more preferably about 750 nm to about 850 nm.

Most preferably, the indicator used is indocyanine green (ICG; purchased for example from Akorn, Decatur or Sigma, St. Louis, Mo.; commercial names: Diagnogreen©, ICGreen©, Infracyanine©, Pulsion©). ICG has been previously been used to study the microcirculation of the eye, the digestive system and liver function (Desmettre, T., J. M. Devoisselle, and S. Mordon. Fluorescence properties and metabolic features of indocyanine green (ICG) as related to angiography. Surv Opthalmol 45, 15-27, 2000). ICG fluoresces intensely when excited at near infrared wavelengths. In the context of this invention, ICG in blood plasma has a peak fluorescence of about 810 to 830 nm with an optimal excitation wavelength of about 780 nm (Hollins, supra; Dorshow, supra). ICG may be advantageous for use in this invention in remains intravascular because it is protein bound. ICG breaks down quickly in aqueous solution, and metabolites are not fluorescent, minimizing recirculation artifact and reducing the time period between which measurements can be made. The wavelength of emission of ICG is also within the optical window (750-1000 nm) in which living tissues are relatively transparent to light.

Other biocompatible fluorescent dyes such as fluorescein and rhodamine would also be suitable in this invention. Fluorescein in blood plasma has a peak fluorescence of about 518±10 nm with an optimal excitation wavelength of about 488 nm (Hollins, supra; Dorshow, supra). Rhodamine in blood plasma has a peak fluorescence of about 640±10 nm with an optimal excitation wavelength of about 510 nm.

Indicator Dosage.

The dosage of indicator is preferably selected such that an amount used is non-toxic to the subject, is present in the circulatory system for an amount of time adequate to establish an indicator concentration curve, but is metabolized in an amount of time such that repeated measurements can be conducted at intervals of about 2-5 minutes apart. Further, the indicator is preferably administered to the subject by injection into a vein.

A dosage of about 0.015 mg/kg is preferable in that this dose leads to peak blood concentrations below 0.002 mg/ml. In this concentration range, the measurement of the circulating indicator concentration is linearly related to the intensity of the emission wavelength detected. For example, in a laboratory animal model, about 0.045 mg can be injected into a 3 kg rabbit (blood volume=200 ml) such that the average circulating concentration is about 0.00023 mg/ml whole blood.

Dye dilution techniques have been applied in humans in other methods and systems using indocyanine green as a dye. Living tissues of humans and animals are relatively transparent for near infrared wavelengths of light which allows for transmission of light across several mm of tissue and transcutaneous detection of the fluorescence emission of ICG. The use of dosages in the ranges stated above is additionally suitable for human use.

Illumination Source.

The illumination sources useful in this invention are preferably selected to produce an excitation wavelength in the near infrared spectrum, preferably about 750 nm to about 1000 nm, and more preferably about 750 to about 850 nm. This selection is advantageous in at least that most tissues are relatively transparent to wavelengths in this range. Thus, in some embodiments, an indicator in the blood stream is excited transcutaneously and indicator emissions detected transcutaneously. Further, blood constituents do not fluoresce at these wavelengths, thus there is no other contributor to the measured fluorescence emission signal. Therefore, this method is advantageous in that at least the sensitivity of detection in this method is improved over other methods, which measure indicator absorption, as opposed to emission.

However, it is within the scope of the invention to use other wavelengths of light, for example in the blue-green or ultraviolet range as some tissues are relatively transparent even at these wavelengths. Selection of the illumination source, therefore, can depend in part on the indicator selected and the tissue from which detection will be made. Preferably, the illumination source is selected to result in the peak emission wavelength of the indicator.

Examples of illumination sources which may be used in this invention include, but are not limited to lamps, light emitting diodes (LEDs), lasers or diode lasers.

In some embodiments, modifications to the system or illumination source may be altered to further to maximize the sensitivity or accuracy of the system for measuring indicator concentration. For example, in some embodiments, the excitation wavelength produced by the illumination source will be steady. Alternatively, the excitation wavelength produced by the illumination source can be modulated to allow for a lock-in detection technique.

For example, the illumination source may emit light in a periodic varying pattern having a fixed frequency and the emission recorded by the photodetector read at the same frequency to improve the accuracy of the readings. The periodic varying pattern and frequency can be selected to improve noise-rejection and should be selected to be compatible with the rest of the instrumentation (such as the light source and photodetector).

The illumination source may be adapted to target a detection area of the subject's tissue from which emission wavelength intensity will be recorded. In some embodiments, the illumination source may comprise an optic fiber for directing the excitation light to the detection area. In some embodiments, the illumination source may comprise mirrors, filters and/or lenses for directing the excitation light to the detection area.

Detection Areas.

The target detection area is that location of a subject's tissue which is exposed to the excitation wavelength of light and/or from which the emission wavelength light intensity output will be measured.

Preferably, the method of detection is non-invasive. In these embodiments, a detection area is selected such that a photodetector can be placed in proximity to the detection area and emission wavelength light intensity measured. Preferably, the photodetector is placed transdermally to at least one blood vessel, but more preferably a highly vascularized tissue area. Examples of detection areas include, but are not limited to fingers, auricles of the ears, nostrils and areas having non-keratinized epithelium (such as the nasal mucosa or inner cheek). In alternative embodiments, the method of detection is minimally invasive. For example, the photodetector can be placed subdermally (within or beneath the epidermis) and proximate to at least one blood vessel or in a perivascular position.

In yet alternative embodiments, the method of detection is minimally invasive. For example, the photodetector can be placed intravascularly to detect indicator emissions, such as within an artery. In such embodiments, an external probe for emitting and receiving light may not be needed. For example, in some embodiments the probe may include a fiber optic located within an intravascular catheter. Specifically, the device may include an intravascular catheter made of biocompatible plastic material which contains, embedded in the catheter wall, an optical fiber 412 that ends at or near the tip 416 of the catheter. For example, the catheter may have a diameter of 100 μm or less. The fiber optic can be used to optically sense the presence and concentration of endogenous substances in the blood or exogenous substances injected or infused in the blood stream through the catheter lumen or another catheter. A fiber optic connector 414 at the proximal external end of the fiber optic connects the fiber to an external monitor. In use, the needle of an injection syringe can be inserted through the catheter lumen and used to inject the indicator material (meanwhile the catheter may be allowed to remain within the vein or artery). The injection needle may be withdrawn from the catheter after injection. After the indicator has been injected and the indicator has had sufficient time to circulate through the cardiovascular system, light from a light source can be directed to the blood and circulated indicator via the optical fiber embedded in the catheter. The optical fiber of the catheter may also be used to receive light from the indicator and transmit the light to the monitor. In alternative embodiments, the catheter may include a plurality of optical fibers for transmitting and/or receiving light used to obtain measure parameters of interest of the cardiovascular system. Catheters that include optical fibers are described in U.S. Pat. Nos. 4,730,622 to Cohen and 5,217,456 to Narciso, the entire contents of each of which are incorporated by reference. In addition, other sensing devices and mechanisms may be included in the intravascular probe.

Additionally, the detection area may be arterialized during indicator emission detection. Examples of conditions resulting in detection area arterializations include, but are not limited to heating or exposure to biologically active agents which effect sympathetic system blockade (such as lidocaine).

Photodetector.

The detection of indicator emissions can be achieved by optical methods known in the art. Measurement of indicator concentration can be made by administering a detectable amount of a dye indicator and using non-invasive, minimally invasive, or intravascular procedures, preferably for continuous detection. The photodetector may be positioned proximately to the detection area of the subject. The photodetector may be positioned distally or proximately to the site of the illumination source.

Fluorescent light is emitted from the indicator with the same intensity for all directions (isotropy). Consequently, in some embodiments, the emission of the dye can be detected both in "transmission mode" when the excitation light and the photodetector are on opposite sides of the illuminated tissue and in "reflection mode" when the excitation and the photodetector are on the same side of the tissue. This is advantageous over other methods at least in that the excitation light and emitted light can be input and detected from any site on the body surface and not only optically thin structures.

Photodetectors which are useful in this invention are those selected to detect the quantities and light wavelengths (electromagnetic radiation) emitted from the selected indicator. Photodetectors having sensitivity to various ranges of wavelengths of light are well known in the art.

In some embodiments, modifications to the system are made to further enhance the sensitivity or accuracy of the system for measuring indicator concentration. For example in some embodiments, the detection system can incorporate a lock-in detection technique. For example, the excitation light may be modulated at a specific frequency and a lock-in amplifier can be used to amplify the output of the photodetector only at that frequency. This feature is advantageous in at least that it further improves the sensitivity of the system by reducing signal to noise and allows detection of very small amounts of fluorescence emission.

In some embodiments a photomultiplier tube is utilized as or operably connected with another photodetector to enhance the sensitivity of the system. Finally, in some embodiments, additional features, such as filters, may be utilized to minimize the background of the emission signals detected. For example, a filter may be selected which corresponds to the peak wavelength range or around the peak wavelength range of the indicator emission.

The detected electromagnetic radiation is converted into electrical signals by a photoelectric transducing device which is integral to or independent of the photodetector. These electrical signals are transmitted to a microprocessor which records the intensity of the indicator emissions as correlated to the electrical signal for any one time point or over time. (For an example of such a device see U.S. Pat. No. 5,766,125, herein incorporated by reference.)

System Calibration.

A) Minimally Invasive Calibration

The method may be minimally invasive in requiring only a single peripheral blood draw from the circulatory system to be taken for calibration purposes. In this invention, indicator concentration is preferably being measured continuously and non-invasively using a photodetector. However, one blood sample from the subject may be withdrawn for calibration of the actual levels of circulating indicator with the indicator levels detected by the system. For example, a blood sample may be drawn from the subject at a selected time after the administration of the indicator into the blood stream. The blood sample may then be evaluated for the concentration of indicator present by comparison with a calibration panel of samples having known indicator concentrations. Evaluation of the indicator concentration may be made spectrophotometrically or by any other means known in the art. Where the subject blood concentration of indicator falls within a range of about 0.001 to about 0.002 mg/ml, the concentration-fluorescence curve is linear and it crosses the origin of the axes, the fluorescence is zero when the concentration is zero.

Therefore a single measurement point suffices to define the calibration curve, and no further blood samples need be taken.

B) Noninvasive Calibration

In another embodiment no blood draw is required for calibration of this system. It is noted that the fluorescence of some indicators, such as ICG, does not substantially vary from patient to patient and that the skin characteristics are relatively constant for large classes of patients. Thus, the fluorescence in the blood of the patient measured from a given site on the body surface can be converted in an absolute measurement of ICG concentration, once the curve of indicator concentration vs. fluorescence is defined for that site of measurement.

Figure 11A:
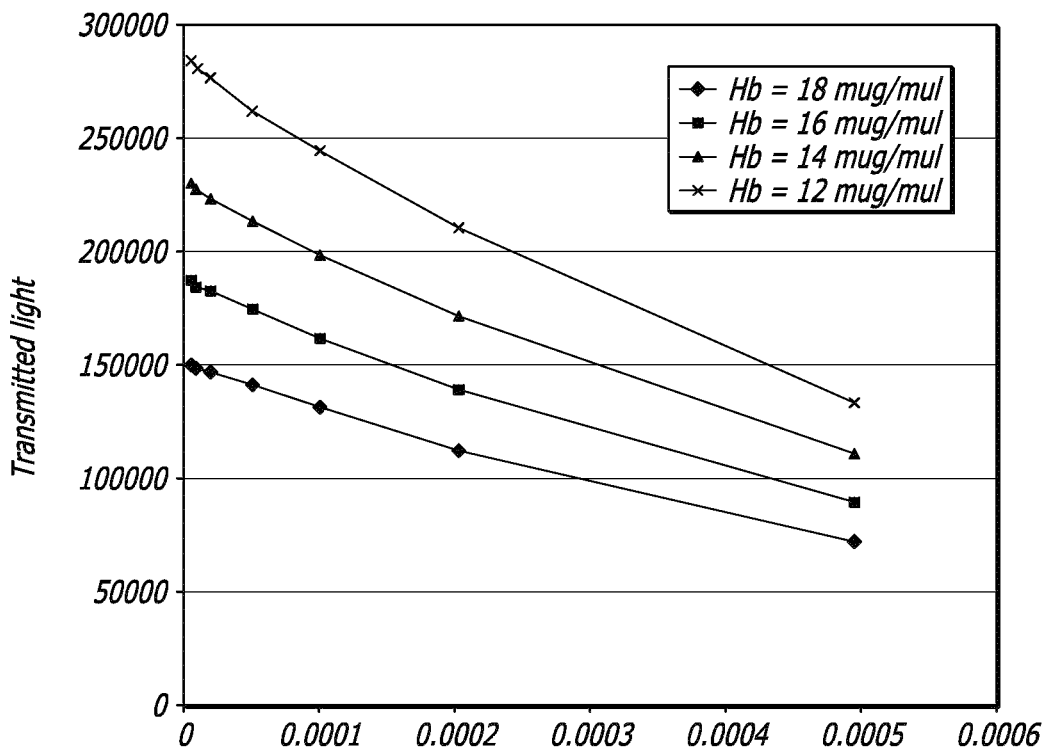
FIGS. 11A-11D are graphs showing calculated transmission and fluorescence signals at 784 nm and 830 nm for different ICG concentrations and hemoglobin contents when absorption coefficients are the same at these two wavelengths.
Figure 11B:
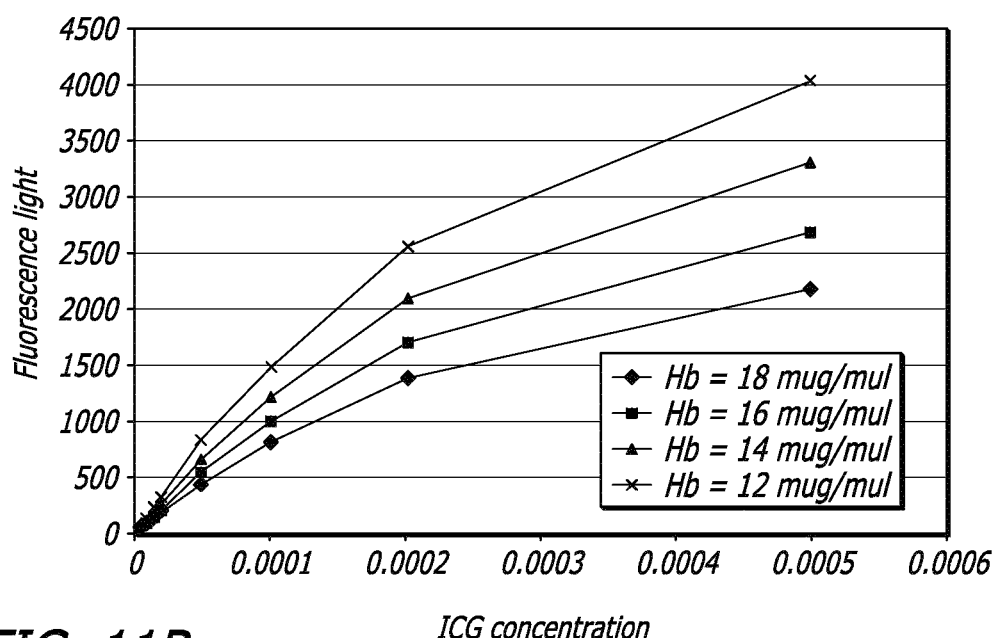
Figure 11C:
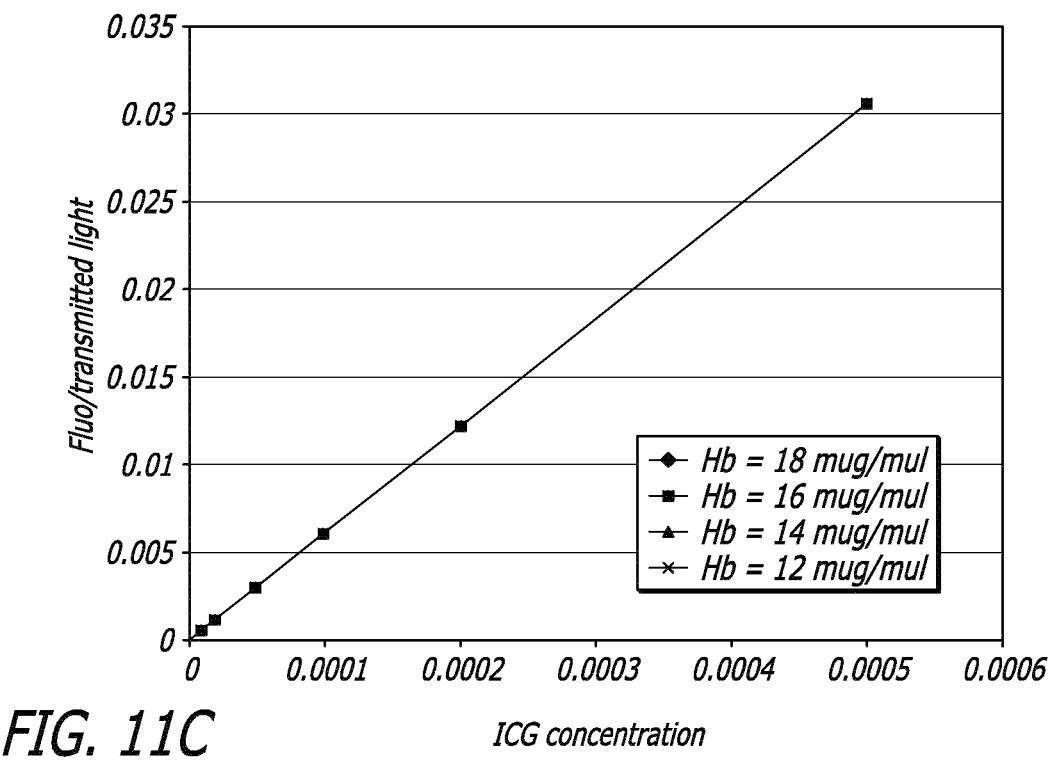

In an exemplary embodiment using noninvasive calibration, the concentration of a fluorescent indicator (ICG) injected in the bloodstream can be determined without taking a blood sample. A probe (including or connected to one or several photodetectors, as described above) can measure the intensity of fluorescent light emitted by the ICG indicator when illuminated by a light source in or near the skin. The probe can also measure the intensity of the light from that source that is reflected by or transmitted through the illumination skin site. Since the ratio of emergent fluorescent light to transmitted excitation light is directly proportional to ICG concentration (see FIGS. 11A-D, FIGS. 12A-12D, and Example 3 below), the concentration of ICG can be determined from the ratio of emergent fluorescent light to transmitted excitation light. For example, the graph in FIG. 11C shows that ICG concentration is directly proportional to the ratio of fluorescent light to transmitted excitation light. In another example illustrated by the graph of FIG. 12C, ICG remains directly proportional to the ratio of fluorescent light to transmitted excitation light even when factoring the variations of absorption properties for hemoglobin (Hb) and ICG with wavelength and the absorption by bloodless tissue. While the slopes of the lines in FIG. 12C vary slightly depending upon hemoglobin content, the differences between the light ratios are relatively small. The ratios may be normalized by creating a table of coefficients that take into account various factors that may affect the light ratios (such as absorption by bloodless tissue, hemoglobin content, path length, skin color, moisture on skin surfaces, body hair, and other factors known to those skilled in the art).

The probe used to transmit and receive light may include a single optical fiber, multiple optical fibers for transmitting and/or receiving light, or other configuration known to those skilled in the art. The excitation light that is received and used in the ratio against fluorescence may be reflected and/or transmitted light. For example, in one embodiment, the light transmitter and receiver can be on the same skin surface so that the receiver can receive light reflected from the tissue. In such an embodiment, the receiving and transmitting element are the same optical fiber (See Diamond et al., "Quantification of fluorophore concentration in tissue-simulating media by fluorescence measurements with a single optical fiber;" *Applied Optics*, Vol. 42, No. 13, May 2003; the contents of which are incorporated herein by reference). In other embodiments, they may be different optical fibers (or other devices known to those skilled in the art). In such embodiments, the various optical fibers may be spatially positioned in relation to each other to optimize measurement, as described in Weersink et al. (See Weersink et al., "Noninvasive measurement of fluorophore concentration in turbid media with a simple fluorescence/reflectance ratio technique;" *Applied Optics*, Vol. 40, No. 34, December 2001; and U.S. Pat. No. 6,219,566 to Weersink et al.; the contents of both of which are incorporated herein by reference). In another embodiment, the transmitter and receiver are positioned substantially opposite each other to allow transmission of the light (such as forward scattering) from the transmitter, through the tissue, and out of the tissue to the receiver on the other side of the tissue.

These methods and systems may be utilized to measure several cardiovascular parameters. Once the system has been calibrated to the subject (where necessary) and the indicator emissions detected and recorded over time, the computing system may be used to calculate cardiovascular parameters including cardiac output and blood volume.

Cardiac Output Calculations.

In some embodiments, the cardiac output is calculated using equations which inversely correlate the area under the first pass indicator emission curve (magnitude of intensity curve) with cardiac output. Cardiac output is typically expressed as averages (L/min). The general methods have been previously described (Geddes, supra, herein incorporated by reference).

Classically, the descending limb of the curve is plotted semi-logarithmically to identify the end of the first pass of indicator. For example, the descending limb of the curve may be extrapolated down to 1% of the maximum height of the curve. The curve can then be completed by plotting values for times preceding the end time. Finally, the area under this corrected curve is established and divided by the length (time) to render a mean height. This mean height is converted to mean concentration after calibration of the detector. The narrower the curve, the higher the cardiac output; the wider the curve, the lower the cardiac output. Several variations of this calculation method are found, including methods that fit a model equation to the ascending and descending portions of the indicator concentration curve.

Depending upon the indicator type and dosage selected, the curve may not return to zero after the end of the first pass due to a residual concentration of indicator recirculation in the system. Subsequent calculations of cardiac output from the curve may then account for this recirculation artifact by correcting for the background emissions, prior to calculating the area under the curve.

Sequential measurements of a cardiovascular circulatory parameter, such as cardiac output or blood volume, may be taken. Each measurement may be preceded by the administration of an indicator to the cardiovascular system. Each measurement may be separated by a time period during which the indicator that was previously administered is substantially eliminated from the circulatory system, for instance by metabolic processes.

To obtain a measurement in absolute physical units, e.g., in liters per minute for cardiac output or liters for blood volume, a blood sample may be taken after each administration of the indicator for calibration purposes, as explained in more detail above.

Another approach may be to take a blood sample only after the first administration of the indicator and to use this blood sample for calibration purposes during each subsequent administration of the indicator and measurement of its resulting fluorescence. However, the operating characteristics of the test equipment may shift during these tests. The optical properties of the tissue being illuminated may also change. The positioning of the illumination source and/or the photo detector may also change. All these changes can introduce errors in the computation of the parameter in absolute physical units when the computations are based on a blood sample that was taken before the changes occurred.

These errors may be minimized by measuring the changes that occur after the blood sample is taken and by then adjusting the measured fluorescence intensity to compensate for these measured changes. This may be accomplished by measuring the intensity of the illumination light after it is transmitted through or reflected by the tissue through which the administered indicator passes. This illumination intensity measurement may be made shortly before, during or shortly after each administration of the indicator. The computations of the cardiovascular parameter that are made during tests subsequent to the first test (when the calibrating blood sample was taken) may then be adjusted in accordance with variations in these illumination intensity measurements.

For example, the computation of the cardiovascular parameter that is made following the second administration of the indicator may be multiplied by the ratio of the illumination intensity measurement made prior to the first administration of the indicator to the illumination intensity measurement made prior to the second administration of the indicator. If the illumination intensity between the first and second measurements doubles, for example, application of this formula may result in a halving of the computation. Other functional relationships between the measured cardiovascular parameter and the illumination intensity measurements may also be implemented.

Any equipment may be used to make the illumination intensity measurements. In one embodiment, the photo detector that detects the fluorescence intensity may also be used to make the illumination intensity measurements. The optical filter that removes light at the illumination frequency may be removed during the illumination intensity measurements. The leakage of the illumination thought this filter may instead be measured and used as the information for the computation.

Another approach to minimizing the number of needed blood samples for a sequence of tests is to take advantage of the known relationship between the amount of indicator that is injected, the volume of blood in the circulatory system and the resulting concentration of the indicator in that blood.

One step in this approach is to determine the volume of blood in the cardiovascular circulatory system using any technique, such as a tracer dilution technique, applied for instance with the Evans Blue dye. The concentration of the indicator after it is administered and mixed throughout the total blood volume, with no offset for metabolic elimination, may then be computed by dividing the amount of the indicator that is administered by the volume of the blood.

Figure 10:
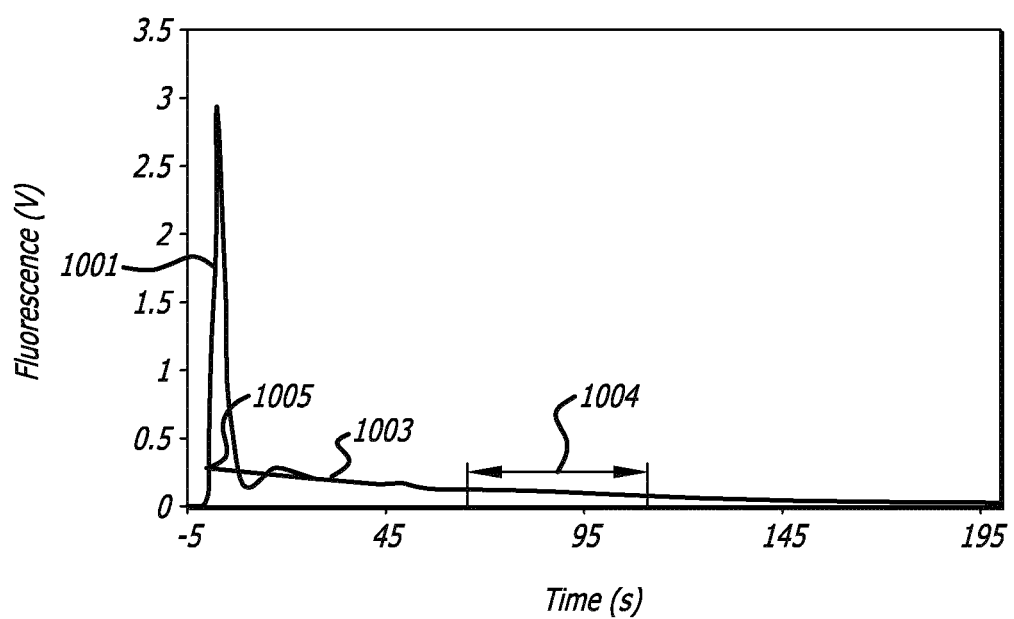
FIG. 10 illustrates a fluorescence intensity curve that includes an extrapolation that intercepts the point on the curve at which the fluorescence is indicative of the concentration of the indicator when mixed throughout the volume of blood of the subject.

The theoretical magnitude of the intensity of the fluorescence from the indicator after the indicator is mixed throughout the total blood volume, without having been metabolized or otherwise eliminated from the circulatory system, may then be determined from the fluorescence curve. FIG. 10 illustrates one way that this may be done, the intensity of the fluorescence of an administered indicator will often rise quickly after the injection, as illustrated by a sharply rising portion 1001. The intensity may then decay slowly, as illustrated by a slowly falling portion 1003. A portion of the curve 1004 during the slow decay may be extrapolated until it intercepts a point 1005 on the fast rising portion. The level of the intensity of the fluorescence at the point 1005 may represent the concentration of the indicator after it is administered and mixed throughout the total blood volume, with no offset for metabolic elimination, i.e., the concentration of the indicator that was computed above.

Based on this extrapolated point, a conversion factor may then be determined that converts the measured intensity of the fluorescence to the concentration of the indicator in the cardiovascular system. The conversion factor may be determined by equating it to the ratio of the concentration of the indicator that was calculated above to the measurement of the intensity of the fluorescence at the intercepted point. The concentration of the indicator at other points on the fluorescence intensity curve shown in FIG. 10 may then be computed by multiplying the measured fluorescence intensity value by the conversion factor.

Subsequent administrations of indicator may be made and measured to monitor the cardiovascular parameter over short or long periods of time. The same computational process as is described above may be used each time to determine the absolute physical value of the desired cardiovascular parameter without having to again take a blood sample. The process may also intrinsically compensate for changes between measurements, other than changes in blood volume, such as changes in the operating characteristics of the test equipment, the optical properties of the tissue being illuminated, and/or the positioning of the illumination source and/or the photo detector.

All of the foregoing computations, as well as others, may be automatically performed by a computing system. The computing system may include any type of hardware and/or software.

Results obtained using this system can be normalized for comparison between subjects by expressing cardiac output as a function of weight (CO/body weight (L/min/kg)) or as a function of surface area (cardiac index=CO/body surface area (L/min/m$^2$)).

Blood Volume Calculations.

In some embodiments, blood volume may be measured independently or in addition to the cardiac output. General methods of measuring blood volume are known in the art. In some embodiments, circulating blood volume may be measured using a low dose of indicator which is allowed to mix within the circulatory system for a period of time selected for adequate mixing, but inadequate or the indicator to be completely metabolized. The circulating blood volume may then be calculated by back extrapolating to the instant of injection the slow metabolic disappearance phase of the concentration curve detected over time (Bloomfield, D. A. Dye curves: The theory and practice of indicator dilution. University Park Press, 1974). Alternative methods of calculation include, but are not limited to those described in U.S. Pat. No. 5,999,841, 6,230,035 or 5,776,125, herein incorporated by reference.

This method and system may be used to examine the general cardiovascular health of a subject. In one embodiment, the method may be undertaken one time, such that one cardiac output and or blood volume measurement would be obtained. In other embodiments, the method may be undertaken to obtain repeated or continuous measurements of cardiovascular parameters over time. Further, repeated measures may be taken in conditions where the cardiovascular system is challenged such that a subject's basal and challenged cardiovascular parameters can be compared. Challenges which may be utilized to alter the cardiovascular system include, but are not limited to exercise, treatment with biologically active agent which alter heart function (such as epinephrine), parasympathetic stimulation (such as vagal stimulation), injection of liquids increasing blood volume (such as colloidal plasma substitutes) or exposure to enhanced levels of respiratory gases.

Figure 1:
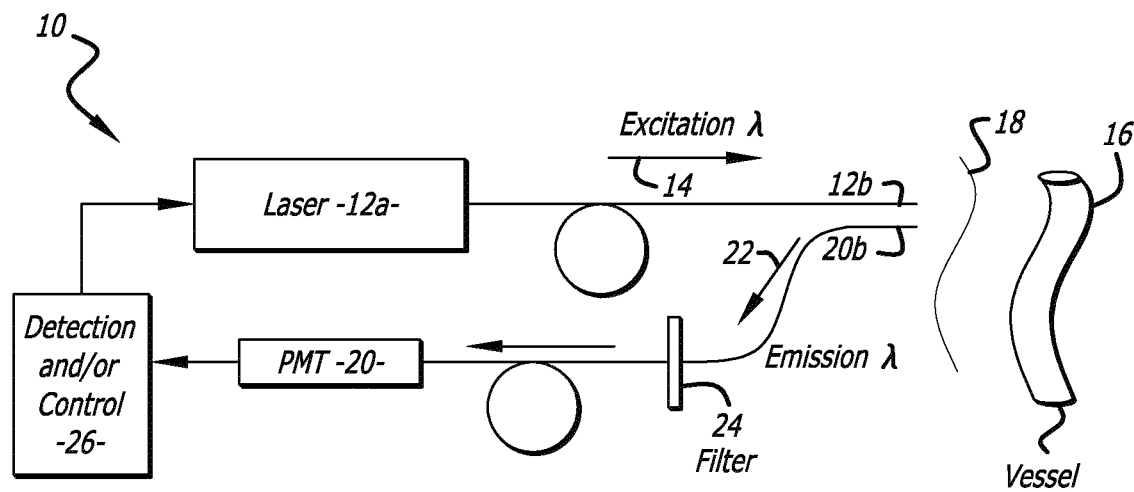
FIG. 1 is a diagrammatic depiction of an example of one embodiment of the system of the present invention.
Figure 2:
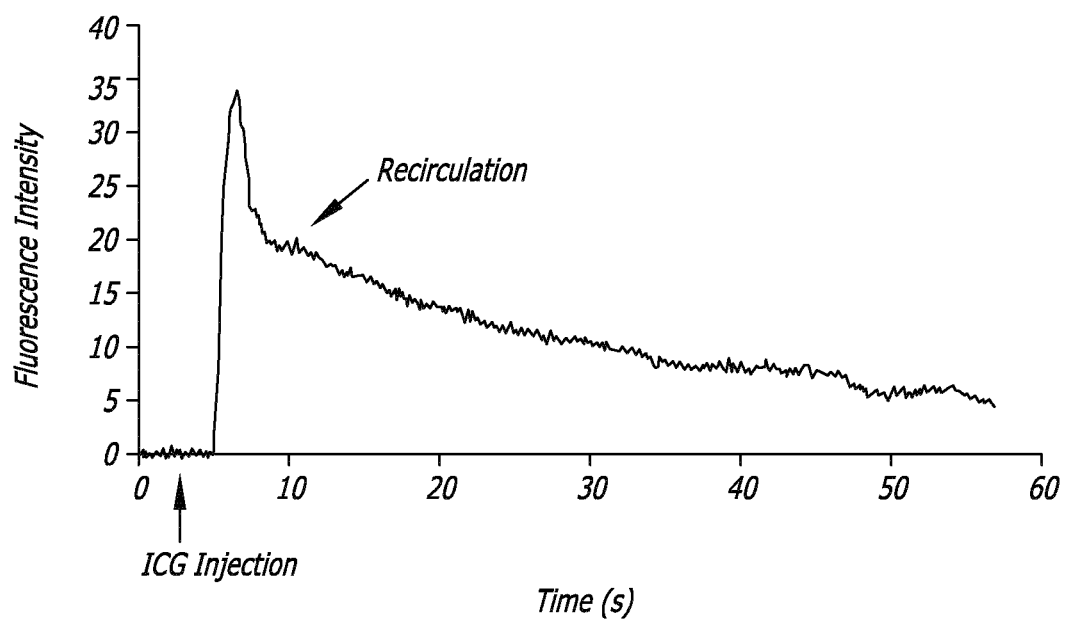
FIG. 2 is a fluorescence intensity curve generated using one embodiment of the present invention.
Figure 3:
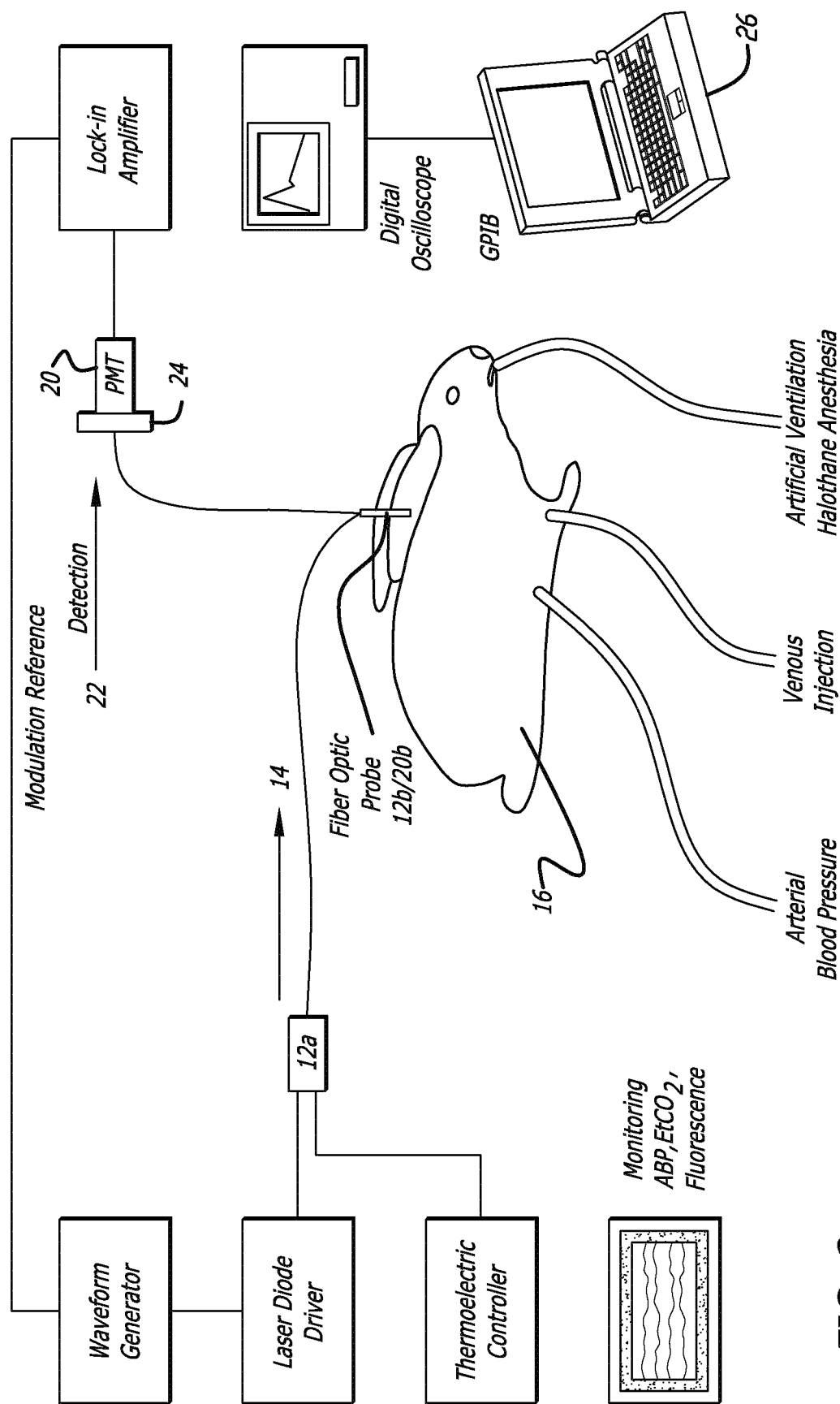
FIG. 3 is a diagrammatic depiction of an example of one embodiment of the present invention having a photodetector positioned on the ear skin surface.

A schematic of one embodiment of a system 10 useful in the present invention is shown in FIG. 1. The system comprises an illumination source 12 here a 775 nm laser selected to emit an excitation wavelength of light 14 which maximally excites ICG, the indicator selected. Here the illumination source 12 is positioned proximately to the subject 16, such that the excitation wavelength of light 14 is shone transdermally onto the indicator circulating in the bloodstream. The system also comprises a photodetector 20 placed in proximity to the subject's skin surface 18 for detection of the indicator emission wavelength 22. Optionally, a filter 24 may be used for isolating the peak wavelength at which the indicator emits, being about 830 nm. Finally, the photodetector 20 is operably connected to a microprocessor 26 for storing the electronic signals transmitted from the photodetector 20 over time, and generating the indicator concentration curve (FIG. 2). Optionally, the microprocessor 26 may regulate the illumination source to coordinate the excitation and detection of emissions from the indicator, for example using a modulation technique. The microprocessor may also comprise software programs for analyzing the output obtained from the detector 20 such that the information could be converted into values of cardiac output or blood volume, for example and/or displayed in the form of a user interface.

In order to demonstrate the utility of the invention, a non-invasive indicator detection system 10 of the invention was used to repeatedly monitor cardiac output. With reference to FIG. 1, a fiber optic 12b transmitted light from illumination source 12a to the subject's skin 18. A second fiber optic 20b, positioned near the skin 18 transmitted the emitted light to a photodetector 20. The indicator was intravenously injected. A body portion which included blood vessels near the surface of the skin was irradiated with a laser. A characteristic fluorescence intensity/concentration curve was obtained upon excitation with laser light at about 775 nm and detection of the fluorescence at about 830 nm. From this information cardiac output and blood volume for the subject was calculated.

The system used for this method may comprise a variety of additional components for accomplishing the aims of this invention. For example, non-invasive detection is described for monitoring of indicators within the circulatory system of the patient. Modifications of the detectors to accommodate to various regions of the patient's body or to provide thermal, electrical or chemical stimulation to the body are envisioned within the scope of this invention. Also, calibration of the system may be automated by a computing system, such that a blood sample is drawn from the patient after administration of the indicator, concentration detected and compared with known standards and/or the emission curve. Also, software may be used in conjunction with the microprocessor to aid in altering parameters of any of the components of the system or effectuating the calculations of the cardiovascular parameters being measured. Further, software may be used to display these results to a user by way of a digital display, personal computer or the like.

A System of Repetitive Measurements of Cardiac Output in Freely Moving Individual During check ups and related procedures, physicians may benefit from observing the cardiac output data of the patient at different times while the patient is performing an exercise routine (i.e. jogging on a treadmill). Therefore, a repeated cardiac output measurement routine is performed on the patient at different heart rates. For example, the first cardiac output of the patient may be measured when the patient is at rest and then at the median and near maximum effort while on the exercise equipment. It may be very inconvenient for the patient to freely move around and perform a given exercise while being wired to a machine. In an alternative embodiment of the present cardiac output systems and methods, the system may comprise a repetitive cardiac output measuring system to collect data from a freely moving individual, such as the exemplary system depicted in FIG. 13. The system may use a method of dye dilution to monitor cardiac output performance in individuals/patients. The system includes two major components. The first component would be worn by the individual as an arm or forearm band/bracelet, and referred to as a calibration and delivery system (or "CDS") 100. The second component may include a sensing device that transmits and receives light of different intensity that may also be worn by the individual, wherein the transmitting and the receiving elements of the device rest against the individual's skin. In an exemplary embodiment, the component may be placed against the individual's ear to target the ear lobe, as depicted by the ear lobe sensor (or "ELS") 111 in FIG. 13. Communication between the CDS and the ELS may either be through a hard wired or a wireless configuration. In either setup the CDS may communicate bidirectionally and wirelessly with a remote external device such as a PDA/laptop/desktop computer 115 through a wireless dongle 112. In the hard wired configuration the CDS may provide power and data storage to the ELS. The CDS may also provide a communication link between the ELS and the dongle 112. In the wireless configuration the ELS would own its power source (i.e. Battery 123) and may communicate directly and wirelessly with the remote dongle.

Figure 13:
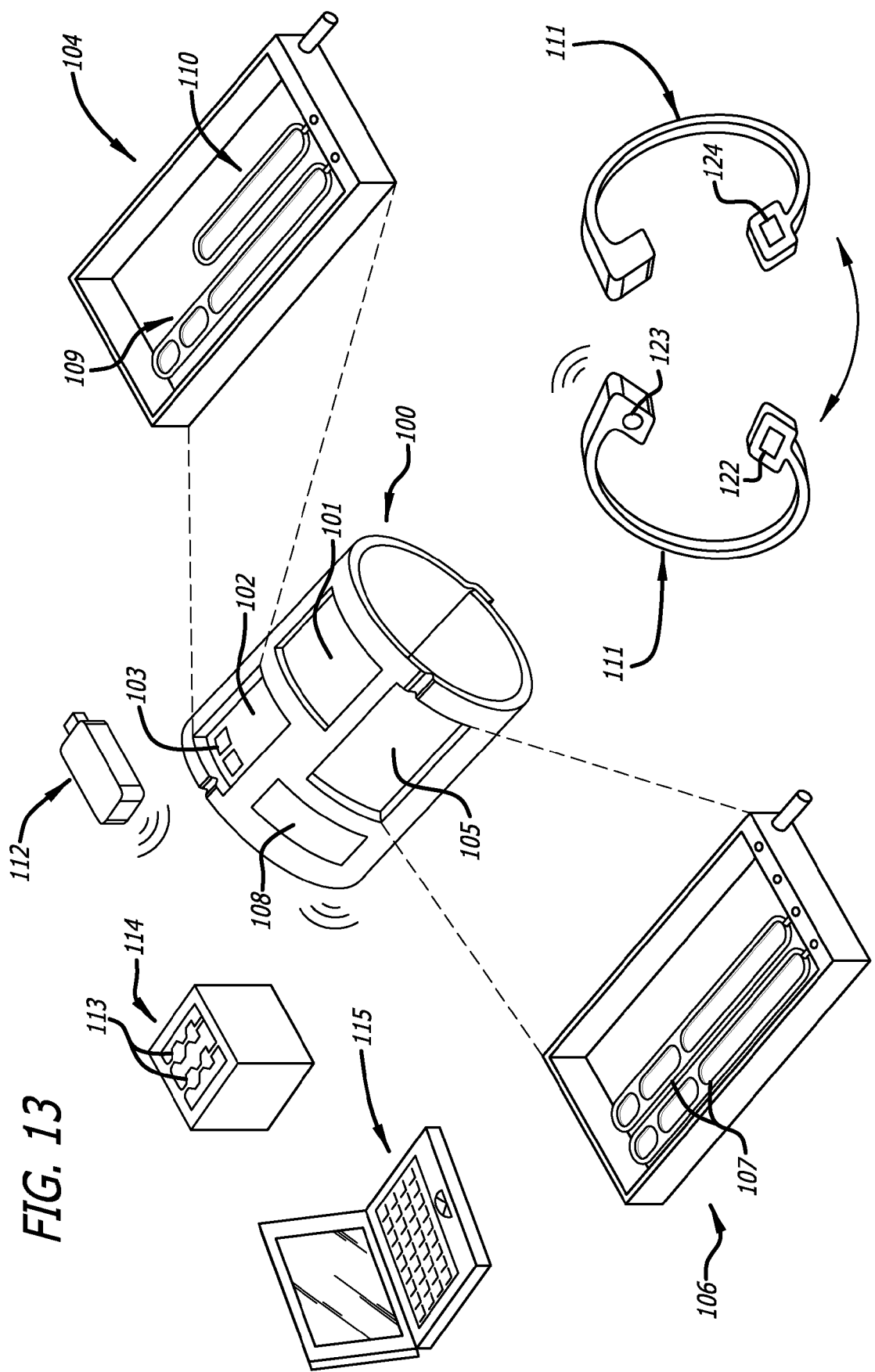
FIG. 13 is a diagrammatic depiction of an alternative embodiment of cardiac output system for repetitive cardiac output measuring of an individual.

The CDS may include circuitry and processing section 101 to control its functions. As depicted in FIG. 13 the CDS may contain the calibration and delivery docking stations 102 and 105, respectively. Theses stations may hold the removable calibration and dye delivery docks 104 and 106, respectively, in place. The calibration dock 104 may hold the calibration cartridge 109 onboard and the dye delivery dock 106 may hold the dye delivery cartridge(s) 107.

Figure 14:
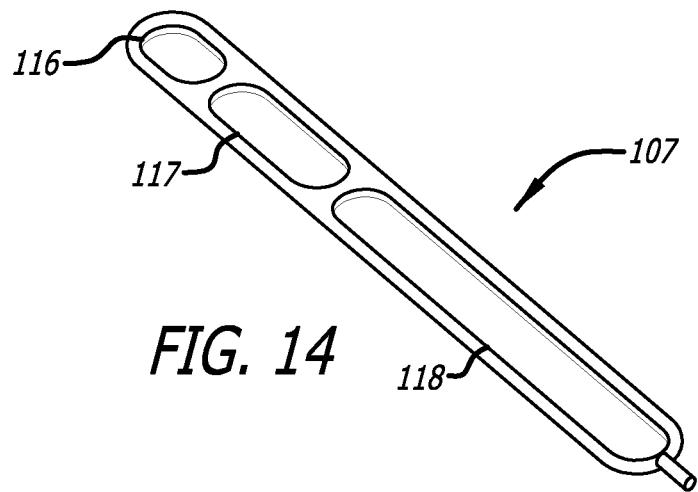
FIG. 14 is an exemplary depiction of a dye delivery cartridge used in the system of FIG. 13.

The exemplary system of FIG. 13 further includes a dye mixing station 114 external to the CDS for preparing the dye delivery cartridge(s) 107 prior to loading on the removable dye delivery dock 106. The mixing station may be equipped with slots 113 to hold cartridge(s). Turing to FIG. 14, a dye delivery cartridge 107 is shown that includes separately sealed chambers 116, 117, and 118 having the dye, sterile water and the sterile saline, respectively. Each of the dye delivery cartridge(s) may be made of a transparent material (i.e. transparent plastic). The area of the cartridge 107 covering the delivery dye may be opaque to block light from reaching the dye. The mixing station may sequentially break the seals in between the chambers, wherein the dye 116 and the sterile water 117 may get mixed first and then the mixture of the two may be mixed with the sterile saline 118.

Figure 15:
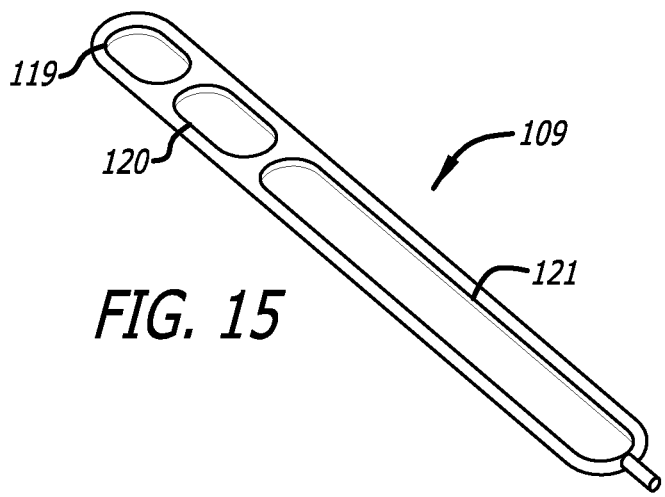
FIG. 15 is an exemplary depiction of a calibration cartridge used in the system of FIG. 13.
Figure 16:
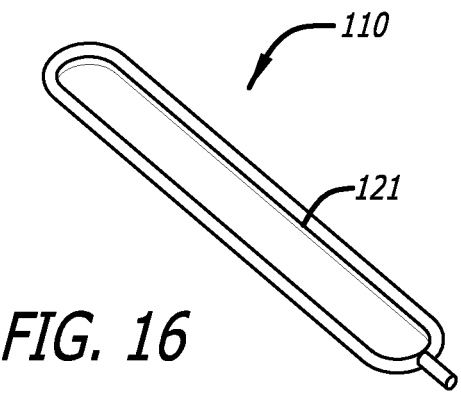
FIG. 16 is an exemplary depiction of a final calibration cartridge used in the system of FIG. 13.

Turning to FIG. 15, a calibration cartridge 109 is depicted that includes sealed chambers 119, 120, and 121 holding the dye, sterile water and an empty chamber "under vacuum", respectively, and may be made of a transparent material as in the dye delivery cartridge. The mixing station 114 may will be configured to break the seals and sequentially mix the dye 119 and the sterile water 120 first, and then the "under vacuum" chamber 121 may be exposed to the mixture. In addition to the calibration cartridge 109, the calibration dock 104 may be loaded with a final calibration cartridge 110 as depicted in FIG. 16. The final calibration cartridge 110 may include one chamber that may be under vacuum and may be used at the end of a typical repetitive cardiac output procedure to draw final blood sample from the individual. The drawn sample, having some concentration of the dye present, may be used to determine the blood volume within the individual's cardiovascular system based on the concentration of the dye.

Both the calibration and dye delivery docks 104 and 106 may contain holders within them for special cartridges that may be attached to valve controlled flow systems that may allow the cartridges to be filled with blood or eject their contents (e.g. through a peristaltic mechanism) into the blood stream.

Referring back to FIG. 13, the electronics 101 of the CDS may provide for bidirectional communication between the cardiac output signals with the ELS and the dongle 112 as well as control programming of the other hardware such as dye delivery dock. The detected fluorescence intensity signal from the ELS 111 that is attached to the individual's ear may be relayed to the dongle 112 through the CDS in the hardwired mode. The signal from the ELS at different dye delivery times may be received by the dongle. The dongle may interpret the received signals to determine the cardiac output of the individual. The data may then be communicated to the external computer for filing or to generate a corresponding profile of the measured cardiac output data of the Individual.

The ELS may include a light emitting element 122 and receiving elements 124 (e.g. a laser diode and a photosensor). The transmitting and receiving elements could either be positioned at opposite sides in transmission mode (as shown with opposite views shown in FIG. 13) or at the same side for reflection mode detection.

Figure 17:
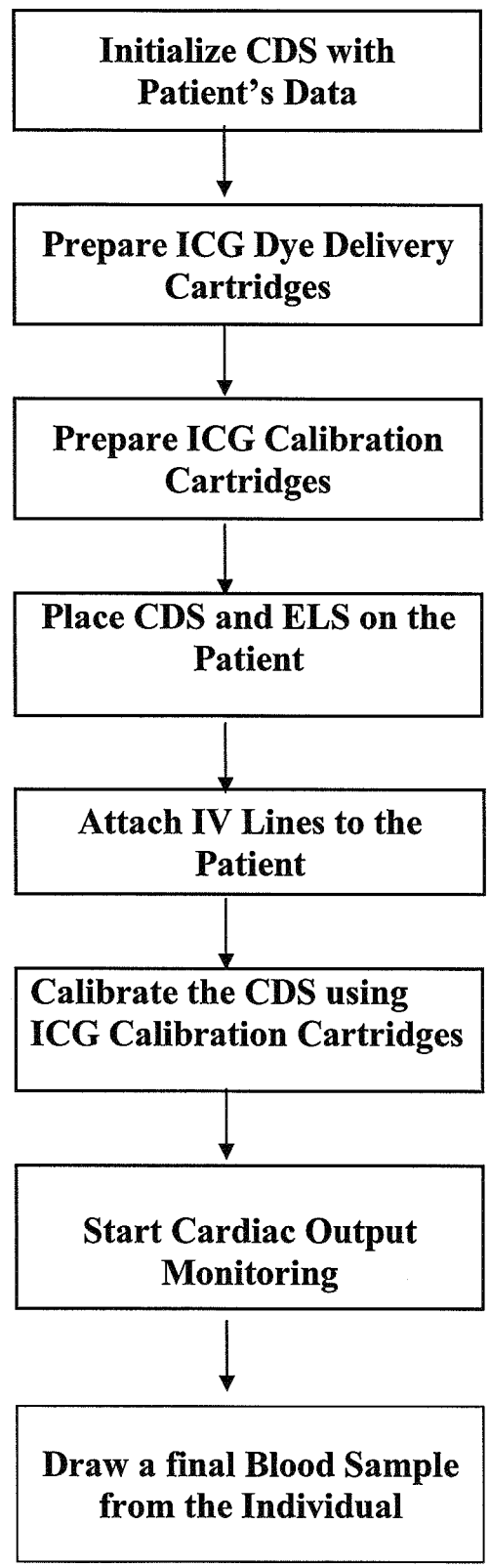
FIG. 17 is flow chart depicting the repetitive cardiac output process of the system of FIG. 13.
Figure 18:
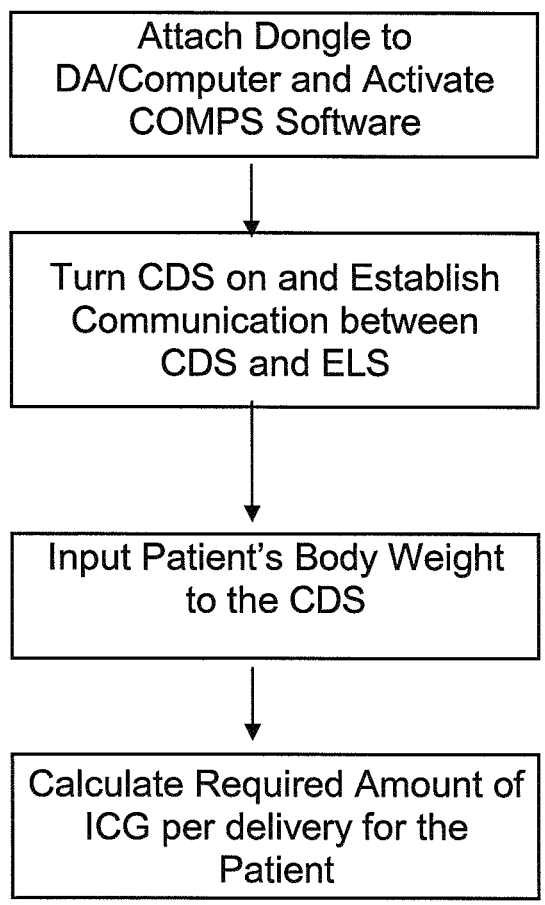
FIG. 18 is a flow chart depicting the CDS initialization process of FIG. 17.

FIG. 17 depicts an exemplary embodiment of repetitive measurement of cardiac output in freely moving individuals using the system of FIG. 13. The process begins by initializing the CDS with the patient's data. This process is shown in FIG. 18. The computer may make a communication link with the CDS through the wireless dongle 112 of FIG. 13. The dongle may contain all the COMPS software necessary for CDS operations, data collection, data interpretation, and maintaining individual's records. The CDS may be in communication with the ELS in the hardwired mode. Based on the weight of the individual the required amount of dye (i.e. ICG) will be determined and filled in each of the dye delivery cartridges.

Figure 19:
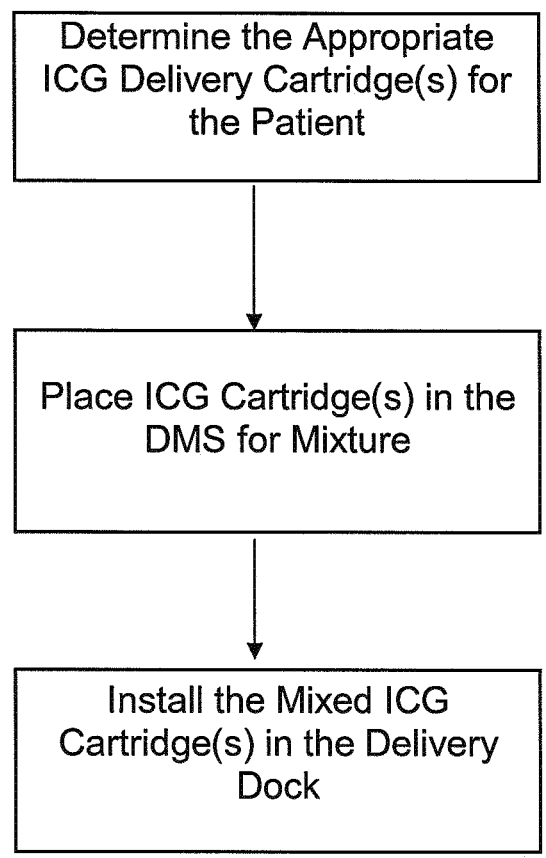
FIG. 19 is a flow chart depicting the preparation process of the dye delivery cartridge of FIG. 17.
Figure 20:
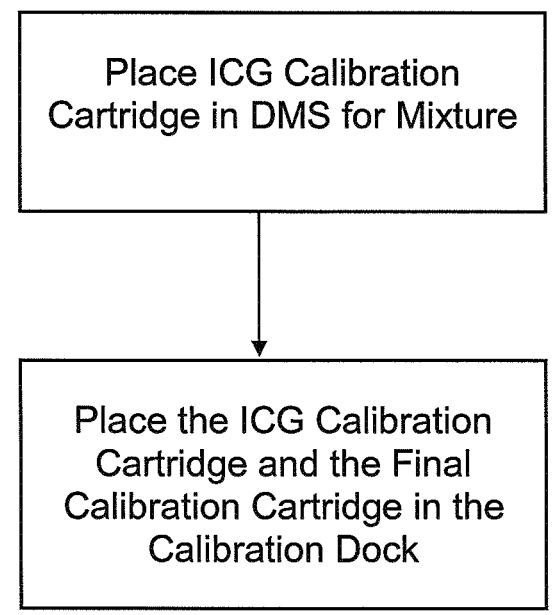
FIG. 20 is a flow chart depicting the preparation process of dye calibration cartridge of FIG. 17.

Returning to FIG. 17, the miniature dye delivery cartridge is prepared, as shown in the block diagram of FIG. 19. Upon determining the appropriate dye amount for each dye delivery cartridge, the cartridge may be loaded on the mixing station 114. As discussed previously, the chambers of the dye delivery cartridge 107 may be mixed in sequence. The mixed cartridge may be transported back to the dye delivery dock of the CDS.

Next, the miniature dye calibration cartridge may be placed on the mixing station 114. The calibration cartridge may also be mixed accordingly in the sequence, as discussed above, and transported to the calibration dye delivery dock.

Turing back to FIG. 17, the CDS and the ELS may be placed on the individual. The CDS may have the calibration and dye delivery docks 104 and 106, respectively, on board having their cartridges loaded.

Figure 21:
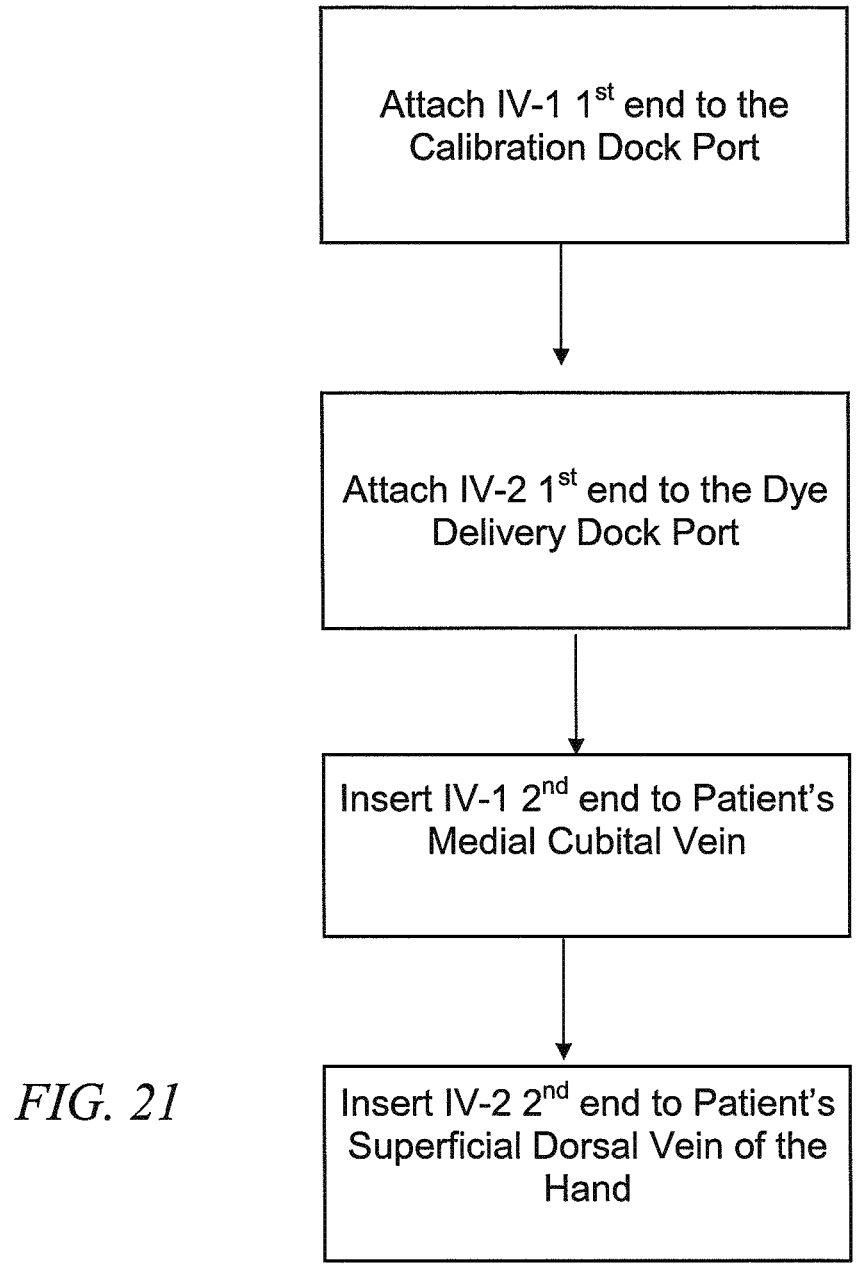
FIG. 21 is a flow chart depicting the IV lines installation procedure of FIG. 17.

Next the IV lines may be attached to the individual/patient. The system may have IV-1 and IV-2 lines to communicate the dye/blood between the individual and the CDS. As shown in the block diagram of FIG. 21 the IV-1 line first end may be attached to the calibration dock port and the other end may be inserted to the individual's vein (i.e. medial cubital vein). Accordingly, the IV-2 line first end may be attached to dye delivery dock port and the opposite end may be inserted to the individual's vein (i.e. superficial dorsal vein of the hand).

Figure 22:
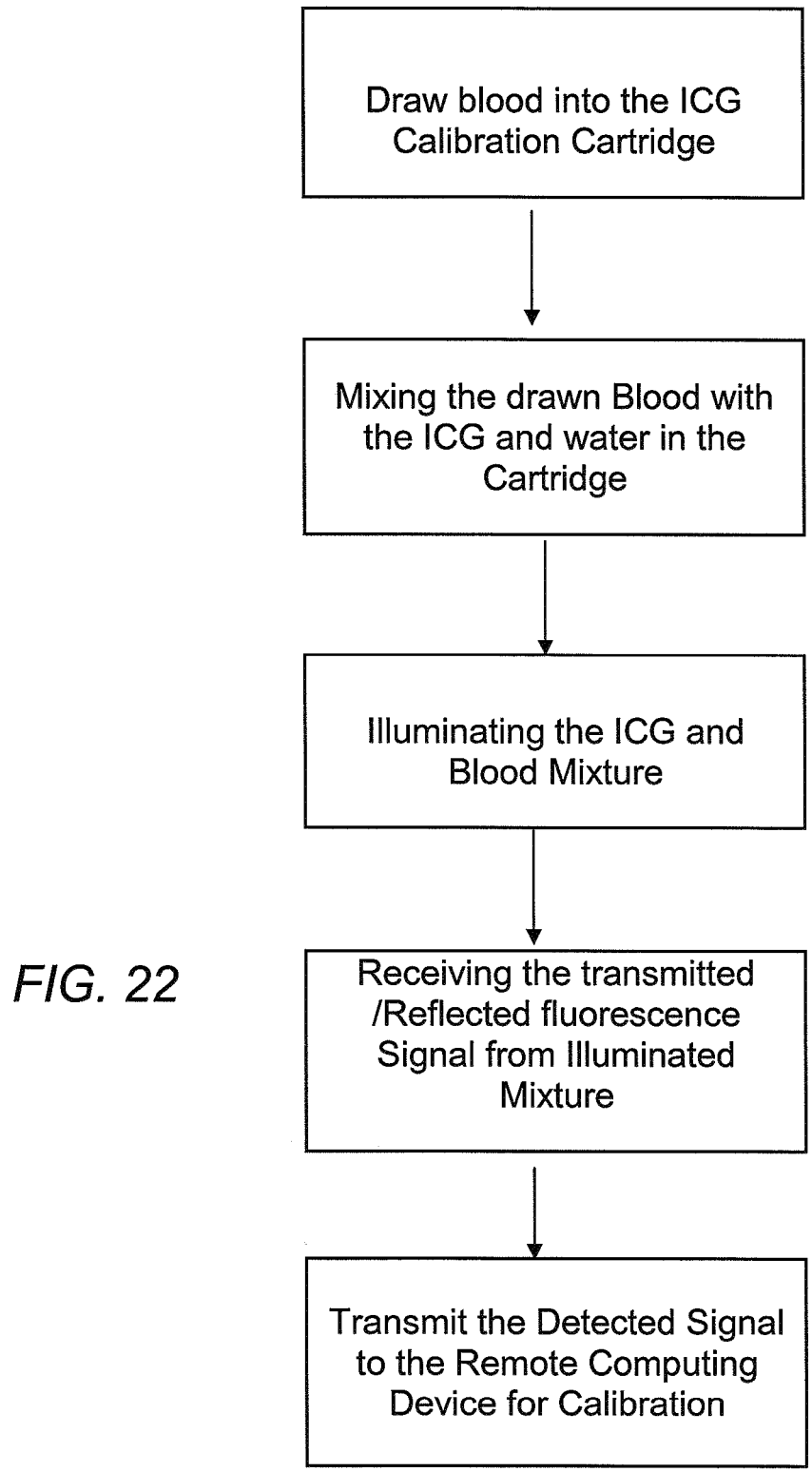
FIG. 22 is a flow chart depicting the CDS calibration process of FIG. 17.

The next step in FIG. 17 is the dye calibration step, wherein the dye in the exemplary embodiment is ICG. FIG. 22 depicts the block diagram of the dye calibration routine. Here the calibration cartridge that was previously loaded into the calibration dock may be used to calibrate the dye fluorescence and it's concentration in the blood sample. The calibration station 131 in CDS may include flaps (not shown) that may act as a fastening gate that holds the calibration dock in the station 131. The calibration docking station may also include plurality of photodetectors 103 located on the bottom of the calibration docking station. The photodetectors may be positioned under the calibration dock and configured to illuminate the transparent calibration and final calibration cartridges placed in the calibration dock. In the exemplary embodiment of the CDS, the photodetectors may be positioned side by side as shown in the station 102.

The flaps placed over the calibration cartridges may include a plurality of light emitting devices such as diodes (LEDs), lasers or diode lasers (not shown). The light emitting elements on the flaps may be positioned directly opposite to the photodetectors in the station. The emitting elements may also be positioned side by side on the flaps directly across the opposing photodetectors 103. The exact location of the light emitting elements and the corresponding photodetectors are not limited to the present exemplary configuration. Their location within the calibration station can easily be interchanged or they may be installed on the side wall of the station rather than at top and bottom. The emitting elements and photodetectors may even be installed on the same side (such as the bottom of the station 102) in the reflection mode calibration.

The calibration step of FIG. 22 may be initiated by drawing a blood sample from the individual through the IV-1 line setup above into the "under vacuum" chamber of the calibration cartridge, which will be mixed with the previously mixed dye. The corresponding light emitting element located over the cartridge may illuminate the mixture and the photodetector may receive the transmitted/reflected fluorescence. Upon receiving the signals the CDS transmits the signals to the external dongle for interpretation.

Figure 23:
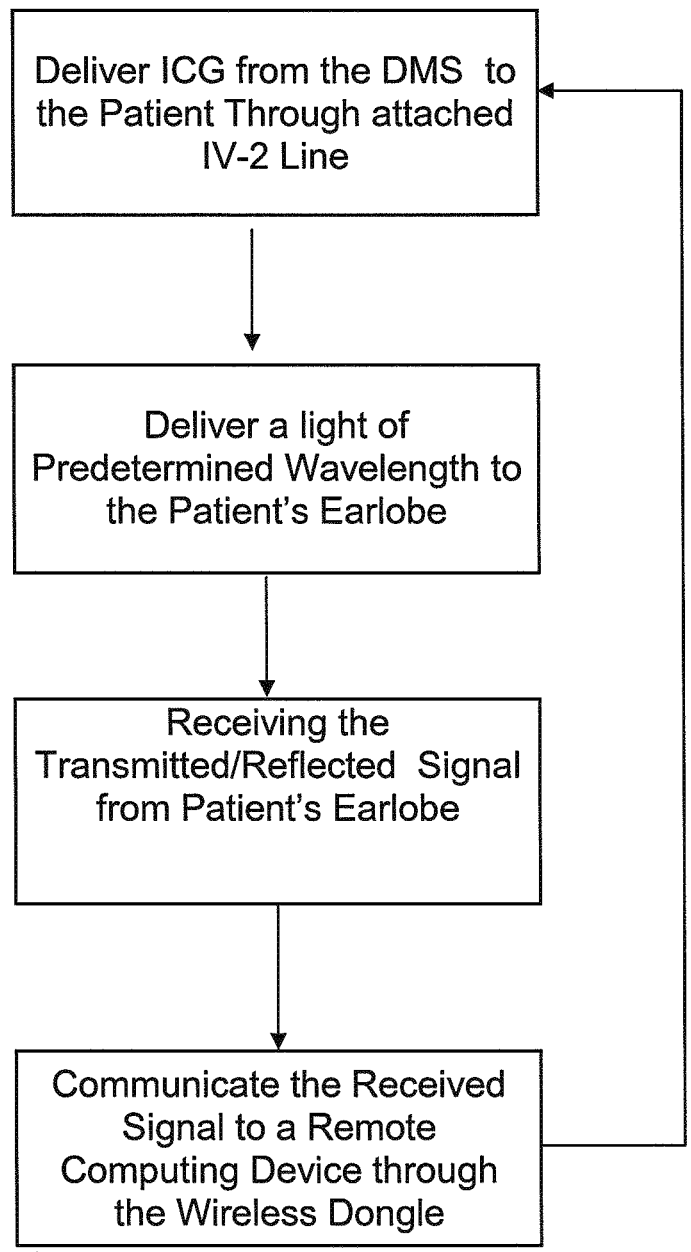
FIG. 23 is a flow chart depicting the cardiac output monitoring process of FIG. 17.

Once the calibration of the dye and its concentration measurement in the blood sample are complete, the next step in FIG. 17 is to initiate the repetitive cardiac output measurement process for the individual. This step is depicted in the routine of the block diagram of FIG. 23.

The dye delivery station starts delivering the dye using the first dye delivery cartridge to the individual's cardiovascular system through the IV-2 line. A predetermined time is set to let the dye concentration reach the target area. The patient's earlobe serves as the target area in this exemplary embodiment. Once the dye has reached the target area, the ELS initiates the transmitting of a predetermined wavelength of light by the transmitting element 122 to the earlobe. The receiver element 124 of the ELS detects the transmitted/reflected fluorescence light from the earlobe. The ELS reads the received signal for a predetermined time once enabled. The signal from the ELS is communicated to the CDS and is further communicated by the CDS to the external dongle 112 of the system of FIG. 13. The dongle may interpret the received signal from the CDS and maintain individual's record. This first dye delivery step may preferably be initiated when the individual is at rest having normal pulse rate.

The next dye injection to the individual's cardiovascular system may be delayed by some time to allow the previously injected dye in the cardiovascular system to be cleared from the circulation. In the exemplary embodiment approximately an approximately five minute wait time may be sufficient to inject the dye from the second dye delivery cartridge. Various wait times may be used in different embodiments. The second dye injection step may be initiated after the individual has reached a higher pulse rate, such as when the heart rate is elevated by 20%. Again as in the first injection, the dongle may receive the fluorescence signal and perform interpretation of the signal to generate the cardiac output value.

In some embodiments, a third dye concentration may be injected from the delivery dock. The wait time for this injection may be longer than that of the second dye injection due to the presence of more concentration of dye present in individual's cardiovascular system and the time for it to be cleared. In this embodiment a 15 minute wait time may be sufficient before administering the third injection. This step may preferably be initiated when the pulse rate of the individual has elevated even higher (for example by 80%).

The repetitive cardiac output measuring process above is not necessarily limited to any type of dye, the wait time before each injection, or the target pulse rate at which the individual is injected with the dye. A skilled practitioner in this field could use the most appropriate dye, wait time and pulse rate for a given application.

The external dongle 114 receiving the signals from the CDS may be able to interpret the cardiac output data and relay them to the external computer to generate a profile of the received data.

In addition to the above repetitive cardiac output measuring process of FIG. 17, after the final injection of dye to the individual a final blood sample may be drawn from the individual into the final cartridge of the calibration dock 104. The corresponding light emitting element on the flaps (not shown) and the photodetector 103 may be enabled. The transmitted/reflected signal may be processed by the CDS and sent to the external dongle. Through this last step the total blood volume of the individual may also be calculated.

The communication and control of the system of FIG. 13 could be accomplished by computer software. The dye release to the individual may either be through initiation of an operator manually or automatically by the system. In automatic dye delivery mode the dye delivery timing may be programmed into the CDS.

The operation of the system of FIG. 13 is not in any way limited to the exemplary embodiment of FIGS. 17-23. The system can operate in more than one way. Various modifications to this embodiment will be readily apparent to those skilled in the art, and the principles defined herein may be applied to other embodiments without departing from the spirit or scope of the system of FIG. 13.

The following examples further illustrate exemplary embodiments of the invention, which are not intended to be limiting.

EXAMPLE 1

Experimental System and Method

An implementation of the system and method of this invention was tested in rats. The excitation source was a 775 nm pulsed diode laser and the fluorescence was detected with a detector being a photomultiplier (PMT) with extended response in the near-infrared range of the spectrum (FIG. 1). Optic fibers were placed in close contact with the skin of the animal's ear for the excitation and detection of the indicator within the blood stream. After injection of a 100 µl bolus of ICG (0.0075 mg/ml) into the jugular vein of a rat, the fluorescence intensity trace (indicator concentration recording) was measured transcutaneously at the level of the rat's ear using reflection mode detection of emissions (FIG. 2).

Calculation of Blood Volume and Cardiac Output.

The initial rapid rise and rapid decay segments of the fluorescence intensity trace represent the first pass of the fluorescent indicator in the arterial vasculature of the animal. Such a waveform is characteristic of indicator dilution techniques. This portion of the recording is analyzed with one of several known algorithms (i.e. Stewart Hamilton technique) to compute the "area under the curve" of the fluorescence intensity trace while excluding the recirculation artifact. Here, the initial portion of the fluorescence trace y(t) was fitted with a model equation $y(t)=y_0 t^\alpha \exp(-\beta t)$ which approximates both the rising and descending segments of the trace. This equation derived from a "tank-in-series" representation of the cardiovascular system has been found fit well the experimental indicator dilution recordings. The numerical parameters of the fit were determined from the approximation procedure, and then the "area under the curve" was computed by numeric integration and used to find the cardiac output with the known formula:

$$Q = \frac{m}{\int_0^\infty C(t)dt} = \frac{\text{amount injected}}{\text{area under the curve}}$$

Back extrapolation of the slow decay segment of the fluorescence intensity trace to the instant when ICG is first detected in the blood (time 0) yields the estimated concentration of ICG mixed in the whole circulating blood volume. By dividing the amount of injected ICG by this extrapolated ICG concentration at time 0, the circulating blood volume was computed.

Calibration Methods.

Indicator concentration C(t) was computed from the fluorescence y(t) using one of two calibration methods. Transcutaneous in vivo fluorescence was calibrated with respect to absolute blood concentrations of ICG, using a few blood samples withdrawn from a peripheral artery after bolus dye injection of ICG. The blood samples were placed in a fluorescence cell and inserted in a tabletop fluorometer for measurement of their fluorescence emission. The fluorescence readings were converted into ICG concentrations using a standard calibration curve established by measuring with the tabletop fluorometer the fluorescence of blood samples containing known concentrations of ICG.

An alternative calibration procedure which avoids blood loss uses a syringe outfitted with a light excitation—fluorescence detection assembly. The syringe assembly was calibrated once before the cardiac output measurements by measuring ICG fluorescence in the syringe for different concentrations of ICG dye in blood contained in the barrel of the syringe. During the measurement of cardiac output, a blood sample was pulled in the syringe during the slow decay phase of the fluorescence trace that is the phase during which recirculating dye is homogeneously mixed in the whole blood volume and is being slowly metabolized. The fluorescence of that sample was converted to concentration using the syringe calibration curve and then related to the transcutaneous fluorescence reading. So long as the ICG concentrations in blood remain sufficiently low (<0.001 mg/ml), a linear relationship can be used to relate fluorescence intensity to concentration.

Either one of these calibration methods can be developed on a reference group of subjects to produce a calibration nomogram that would serve for all other subjects with similar physical characteristics (i.e., adults, small children etc.). This is advantageous over prior methods at least in that an additional independent measurement of the blood hemoglobin concentration for computation of the light absorption due to hemoglobin is not required.

EXAMPLE 2

A. A Sample Method and System for Measuring Cardiac Output and Blood Volume

Figure 4:
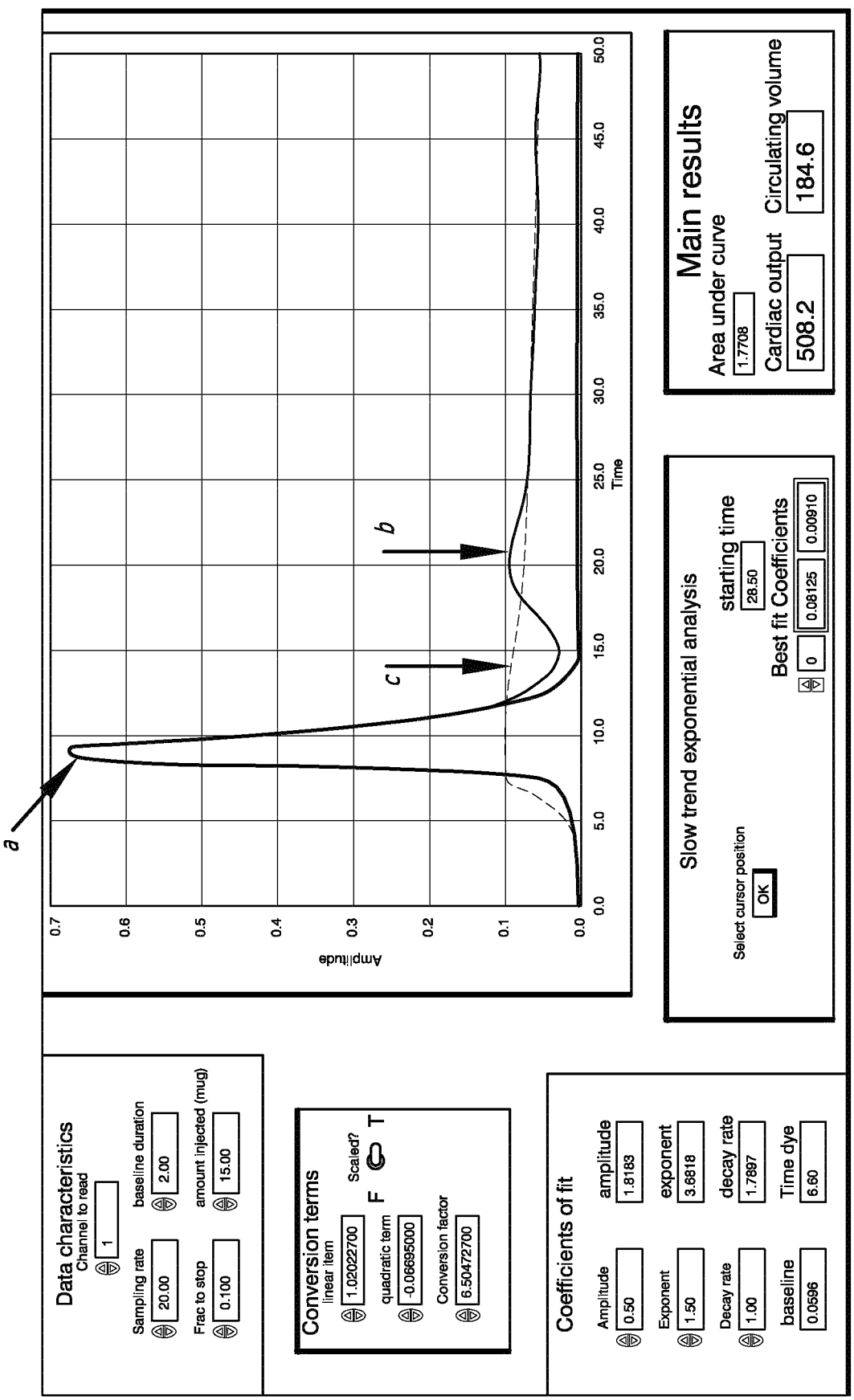
FIG. 4 is a diagrammatic depiction of a user interface of a cardiac output computer program useful in conjunction with this invention. The interface may depict information regarding values measured and converted from fluorescence to concentration, and parameters of the curve fit for the values obtained using the method or system.

Experiments have been performed in New Zealand White rabbits (2.8-3.5 Kg) anesthetized with halothane and artificially ventilated with an oxygen-enriched gas mixture (FiO$_2$~0.4) to achieve a SaO2 above 99% and an end-tidal CO$_2$ between 28 and 32 mm Hg (FIG. 4). The left femoral artery was cannulated for measurement of the arterial blood pressure throughout the procedure. A small catheter was positioned in the left brachial vein to inject the indicator, ICG. Body temperature was maintained with a heat lamp.

Excitation of the ICG fluorescence was achieved with a 780 nm laser (LD head: Microlaser systems SRT-F780S-12) whose output was sinusoidally modulated at 2.8 KHz by modulation of the diode current at the level of the laser diode driver diode (LD Driver: Microlaser Systems CP 200) and operably connected to a thermoelectric controller (Microlaser Systems: CT15W). The near-infrared light output was forwarded to the animal preparation with a fiber optic bundle terminated by a waterproof excitation-detection probe. The fluorescence emitted by the dye in the subcutaneous vasculature was detected by the probe and directed to an 830 nm interferential filter (Optosigma 079-2230) which passed the fluorescence emission at 830±10 nm and rejected the retro-reflected excitation light at 780 nm. The fluorescence intensity was measured with a photomultiplier tube (PMT; such as Hamamatsu H7732-10 MOD) connected to a lock-in amplifier (Stanford Research SR 510) for phase-sensitive detection of the fluorescence emission at the reference frequency of the modulated excitation light. The output of the lock-in amplifier was displayed on a digital storage oscilloscope and transferred to a computer for storage and analysis.

In most experiments, one excitation-detection probe was positioned on the surface of the ear arterialized by local heating. In some studies, the laser emission beam was separated in two beams with a beam splitter and directed to two measurement sites (ear skin and exposed right femoral artery). Two detection systems (PMT+lock in amplifier) were used for measurement of the fluorescence dilution traces from the two sites. In all experiments, a complete record of all experimental measurements (one or two fluorescence traces, arterial blood pressure, end-tidal CO$_2$, Doppler flow velocity) was displayed on line and stored for reference.

Calculations.

A LabView program was used to control the oscilloscope used for sampling the fluorescence dilution curves, transfer the data from the oscilloscope to a personal computer and analyze the curves online for estimation of the cardiac output and circulating blood volume. As shown on the program user interface (FIG. 5), the measured fluorescence dilution trace (a) is converted to ICG blood (b) using the calibration parameters estimated as described in the next section of this application and fitted to a model: $C(t)=C_0 t^\alpha \exp(-\beta t)$.

The model fit is performed from the time point for which the fluorescent ICG is first detected to a point on the decaying portion of the trace that precedes the appearance of recirculating indicator (identified from the characteristic hump after the initial peak in the experimental trace). The model equation is used to estimate the "area under the curve" for the indicator dilution trace. The theory of indicator dilution technique predicts that the area under the concentration curve is inversely proportional to the cardiac output (Q):

$$(Q) = \frac{m}{\int_0^\infty C(t)dt}$$

Where m is the mass amount of injected indicator and c(t) is the concentration of indicator in the arterial blood at time t. The program also fits the slow decaying phase of the measurement to a single exponential to derive the circulating blood volume from the value of the exponential fit at the time of injection. For the experimental ICG trace shown in FIG. 4, the estimated cardiac output is 509 ml/min and the circulating blood volume is 184 ml, in the expected range for a 3 Kg rabbit. This computer program is advantageous in that it improved the ability to verify that the experimental measurements are proceeding as planned or to correct without delay any measurement error or experimental malfunction.

Indicator Dosage.

In this experiment is was found that a dose of about 0.045 mg injected ICG was optimal in this animal to allow for detection of an intense fluorescence dilution curve and at the same time rapid metabolic disposal of the ICG. Further, with this small dose cardiac function measurements could be performed at about intervals of 4 minutes or less.

Detector Placement.

Defined fluorescence readings were obtained by positioning the detection probe above the skin surface proximate to an artery or above tissue, such as the ear or the paw arterialized by local heating.

B. Calibration of Transcutaneous Indicator Intensity and Circulating Indicator Concentration Calibration of the transcutaneous fluorescence intensity measured at the level of the animals' ear as a function of ICG concentration in blood was performed as follows. A high dose of ICG (1 mg) was injected intravenously and equilibrated homogeneously with the animal's total blood volume in about a one minute period. At equilibrium, the blood ICG concentration resulting from this high dose is several times larger than the peak ICG concentration observed during the low dose ICG injections (0.045 mg) used to measure the cardiac output. In this way, a calibration curve was created that accommodated the full range of ICG concentrations observed during the cardiac function measurements.

As the liver metabolizes ICG, the blood ICG concentration decreases back to 0 in about 20 minutes. During that time period, 5 to 8 blood samples (1.5 ml) were withdrawn from the femoral artery and placed in a pre-calibrated blood cuvette. The fluorescence intensity of the blood in the cuvette was converted to a measurement of concentration using the known standard curve of fluorescence intensity versus ICG concentration established for the cuvette. ICG fluorescence was measured at the level of the ear at the exact time of the blood sample withdrawal. Because ICG is homogeneously equilibrated in the animal's blood volume, when the blood samples are withdrawn, the fluorescence intensity measured at the level of the ear corresponds directly to the ICG blood concentration at the time of the measurement and therefore the ICG concentration determined from the cuvette reading. As this example shows, transcutaneous ICG fluorescence is proportional to blood ICG concentration such that a single blood withdrawal can suffice to find the proportionality factor between the two quantities.

Figure 5:
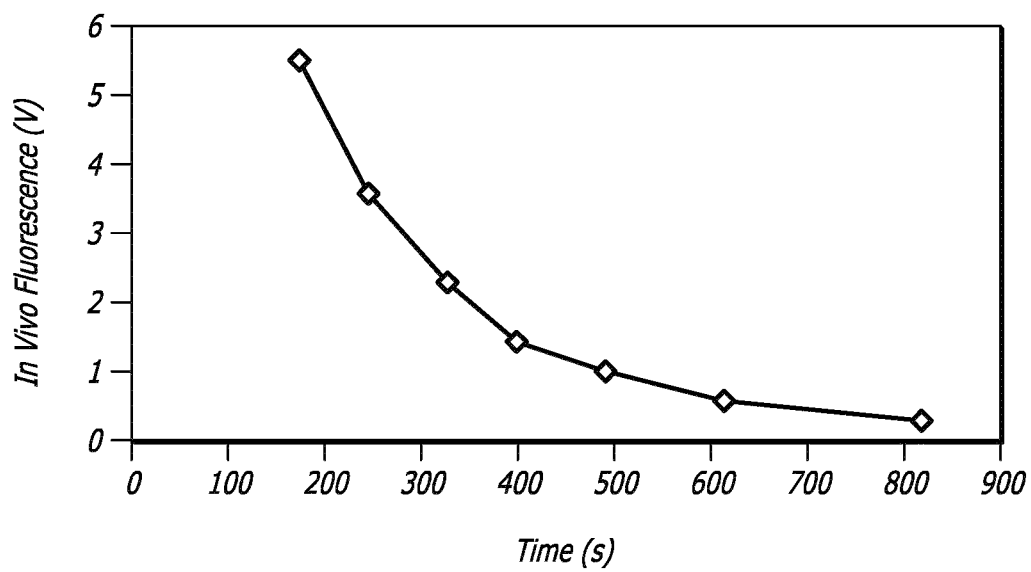
FIG. 5 is a depiction of a decay of fluorescence intensity curve as a function of time following injection of a 1 mg dose of indocyanine green (ICG) in an experimental animal.
Figure 6:
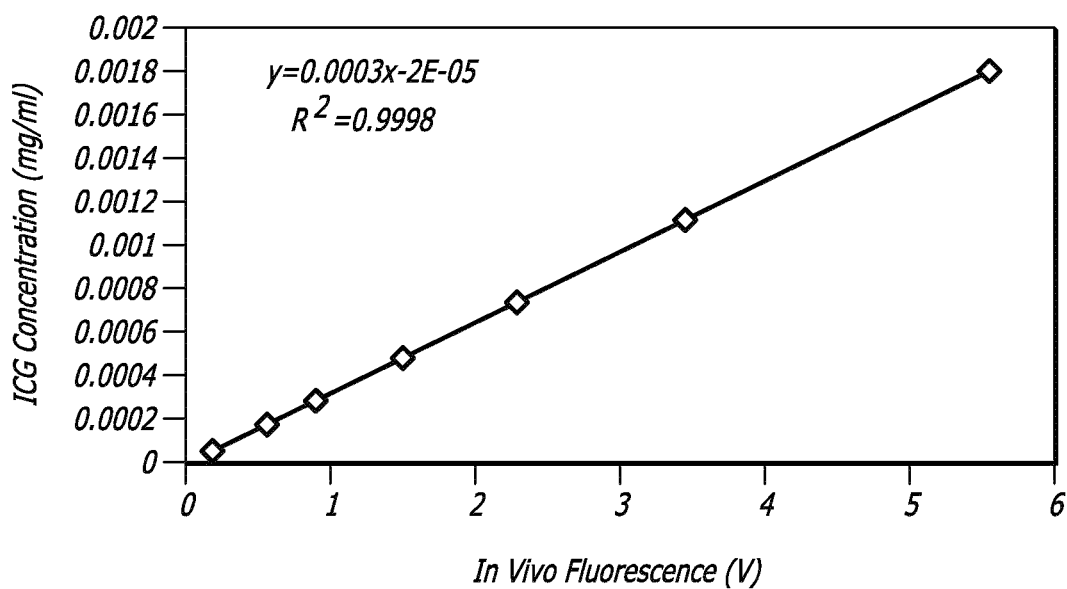
FIG. 6 is a depiction of a calibration curve for blood ICG concentration as a function of transcutaneous ICG fluorescence.

As shown in FIG. 5, the transcutaneous ear fluorescence intensity (in V) as a function of time (in s) after the high dose (1 mg) ICG injection during the calibration sequence. FIG. 5 shows the characteristic first order exponential decay of ICG in blood as the dye is being metabolized. FIG. 6 shows the ICG concentration (in mg/ml) as a function of the in vivo fluorescence for the same example and the same time points. For the range of concentrations used in these studies, ICG concentration and transcutaneous fluorescence were linearly related. The calibration line passes through the origin of the axes since there is no measured fluorescence when the ICG blood concentration is 0.

Thus, a simple proportionality factor exists between blood ICG concentration and transcutaneous fluorescence. This feature of the fluorescence dilution technique measuring light emission is advantageous over the conventional dye dilution technique based on ICG absorption which requires light absorption caused by ICG to be separated from light absorption by tissue and blood. After the proportionality factor is determined, ICG fluorescence dilution profiles can only then are converted into concentration measurements for computation of the cardiac output using the indicator-dilution equation.

Results of Cardiac Output Measurements.

Calibrated cardiac output readings have been obtained in 8 animals (body wt: 3.0±0.2 Kg). The following table lists the values during baseline conditions. The values are presented as the mean±standard deviation of three consecutive measurements obtained within a 15 min period.

TABLE 1

| Exp. | Cardiac output (ml/min) |
|---|---|
| 1 | 530 ± 15 |
| 2 | 500 ± 17 |
| 3 | 370 ± 12 |
| 4 | 434 ± 16 |
| 5 | 481 ± 6 |

The average for the five experiments (463 ml/min) is in order of reported cardiac outputs (260-675 ml/min) measured with ultrasound or thermodilution techniques in anesthetized rabbits (Preckel et al. Effect of dantrolene in an in vivo and in vitro model of myocardial reperfusion injury. Acta Anaesthesiol Scand, 44,194-201, 2000. Fok et al. Oxygen consumption by lungs with acute and chronic injury in a rabbit model. Intensive Care Med, 27, 1532-1538, 2001). Basal cardiac output varies greatly with experimental conditions such as type of anesthetic, duration and depth of anesthesia, leading to the wide range of values found in the literature. In this example, the variability (standard deviation/mean) of the calculated cardiac output with fluorescence dilution is ~3% for any triplicate set of measurements which compares favorably with the reported variability for the thermodilution technique (~5-10%).

C. Comparison of Measurements Obtained by Fluorescence Dilution Cardiac Output Method Via Transcutaneous Measurement and Subcutaneous Measurement Experimental Methodology The experimental preparation described in the preceding section (Example 2) includes two measurement sites for the fluorescence dilution traces: a transcutaneous site at the level of the ear central bundle of blood vessels and the exposed femoral artery. The ear vasculature is arterialized by local heating. With this preparation, the cardiac output estimates obtained from the peripheral non-invasive (transcutaneous) measurement site were compared with estimates obtained by interrogating a major artery.

The intensity of the fluorescence signal at the level of the exposed femoral artery during the slow metabolic disappearance phase of the injected ICG is compared to the calibrated ear fluorescence measurement to derive a calibration coefficient (arterial ICG fluorescence into ICG blood concentration). In this way cardiac output estimates expressed in ml/min were derived from the two sites.

Results.

Figure 8:
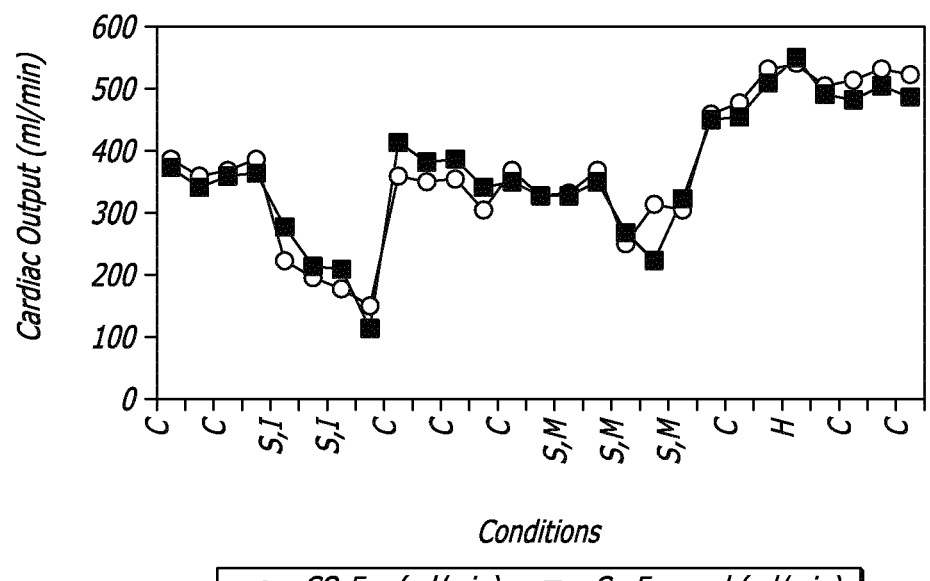
FIG. 8 is a depiction of cardiac output measurements derived from sites on the ear surface and on the exposed femoral artery during one experiment.

FIG. 8 shows the time course of the cardiac output measurements obtained from the ear site and from the exposed femoral artery in a representative experiment during control conditions (C), intense then mild vagal stimulation (S, I and S, M), and post-stimulation hyperemia (H). Near-identical estimates of the cardiac output are obtained from the two sites during all phases of the study.

The relationship between cardiac output derived from measurement of the fluorescence dilution curve at the level of the skin surface (COskin, in ml/min) and at the level of the exposed femoral artery (COfem, in ml/min) was investigated. The linear relationships between the two measures are summarized in the table below:

TABLE 2

| Exp. | Linear regression | Regression Coef. | Number measurements |
|---|---|---|---|
| 1 | COskin = 0.65 (±0.11) * COfem + 145.0 (±54.0) | 0.81 | 22 |
| 2 | COskin = 1.01 (±0.06) * COfem + 2.0 (±22.0) | 0.96 | 27 |
| 3 | COskin = 1.05 (±0.14) * COfem − 56.0 (±54.0) | 0.91 | 13 |

The two measures of fluorescence cardiac output are tightly correlated. In the last two experiments, the slope of the regression line is not statistically different from 1.0 and the ordinate is not different from 0.0 indicating that the two measurements are identical. These observations suggest that fluorescence dilution cardiac output can be reliably measured transcutaneously and from a peripheral site of measurement that has been arterialized by local application of heat. Attenuation of the excitation light and ICG fluorescence emission by the skin does not prevent the measurement of well-defined dye dilution traces that can be analyzed to derive the cardiac output.

While the specification describes particular embodiments of the present invention, those of ordinary skill can devise variations of the present invention without departing from the inventive concept.

D. Comparison of Measurements Obtained by Fluorescence Dilution Cardiac Output Method and Doppler Flow Velocity Technique Experimental Methodology.

The present method was compared with an ultrasonic Doppler velocity probe method to record cardiac output measurements. In this example the above procedure was modified in that, the animal's chest was opened with a median incision of the sternum and a 6 mm 20 MHz Doppler velocity probe was gently passed around the ascending aorta and tightened into a loop that fits snuggly around the aorta.

For detection of the fluorescent detection of the indicator, two illumination+detection fiber optic probes were used: one probe was placed on or above the ear middle vessel bundle and the other probe was placed in proximity to the dissected left femoral artery. Local heating to 42 degrees centigrade arterialized the ear vasculature.

Figure 7:
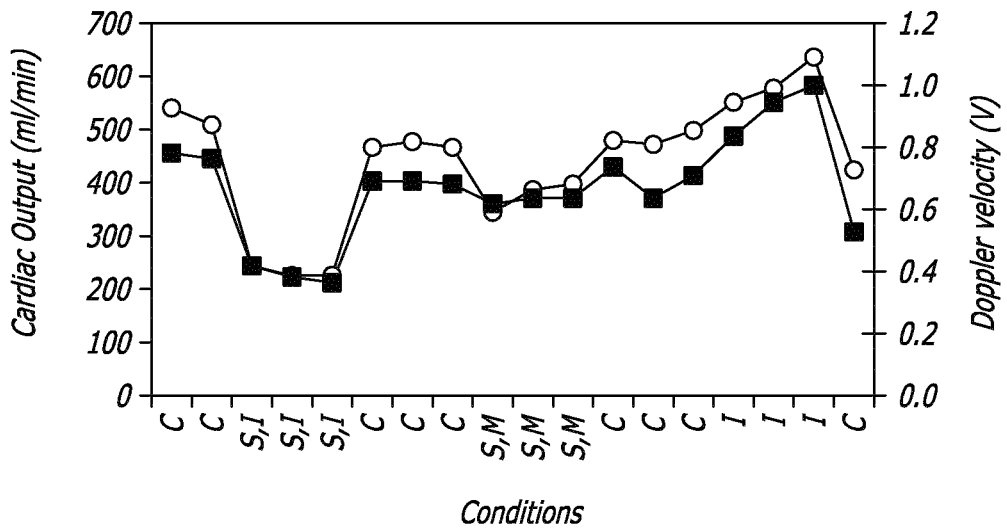
FIG. 7 is a depiction of cardiac output and aortic velocity measurements during one representative experiment.

In this example, two maneuvers were used to change the cardiac output from its control level: vagal stimulation, which reduces the cardiac output, and saline infusion, which increases the circulating volume and cardiac output. The right vagal nerve was dissected to position a stimulating electrode. Stimulation of the distal vagus results in a more or less intense decrease of the heart rate that depends on the stimulation frequency and voltage (1 ms pulses, 3 to 6 V, 10 to 30 Hz). The cardiac output and aortic flow velocity also decrease during vagal stimulation even though less markedly than the heart rate decreases because the stroke volume increases. Saline infusion at a rate of 15-20 ml/min markedly increases the cardiac output. FIG. 7 shows the time course of the cardiac output and aortic velocity measurements in one experiment including control conditions (C), intense then mild vagal stimulation (S, I and S, M), and saline infusion (I).

Results.

There is consistent tracking of the Doppler aortic velocity by the fluorescence dilution cardiac output measurement. The relationship between fluorescence dilution cardiac output and aortic Doppler flow velocity was investigated in four rabbits. The linear relationships between fluorescence dilution cardiac output (CO, in ml/min) and aortic flow velocity signal (VAor, not calibrated, in Volts) are summarized in the table:

TABLE 3

| Exp. | Linear regression | Regression Coef. | Measurements |
|---|---|---|---|
| 1 | CO = 789 (±123) * VAor + 166 (±34) | 0.79 | 27 |
| 2 | CO = 607 (±62) * VAor + 50 (±32) | 0.90 | 24 |
| 3 | CO = 614 (±64) * VAor − 45 (±38) | 0.90 | 27 |
| 4 | CO = 654 (±41) * VAor − 3 (±29) | 0.97 | 18 |

This data indicates that the fluorescence dilution cardiac output is highly correlated with aortic flow velocity as indicated by the elevated regression coefficient ($\geqq 0.9$ in 3 experiments). Further, the slopes of the linear regression lines between fluorescence dilution cardiac output and aortic flow velocity are similar and statistically not different in the four studies. This suggests a constant relationship between the two variables across experiments. The ordinates of regression lines are not different from 0 in the last three experimental studies, which suggests absence of bias between the two measures of aortic flow.

The results above establish that fluorescence dilution cardiac output measured transcutaneously tracks the Doppler flow velocity measured in the ascending aorta.

EXAMPLE 3

Comparison with Thermodilution Method

Experimental Methodology.

Other experiments were performed in New Zealand White rabbits using the methodology described for the preceding example 2. In addition, a 4F thermodilution balloon catheter was inserted into the right femoral vein and advanced until the thermistor reached the main pulmonary artery. Correct placement of the catheter tip was verified visually through the thoracotomy. The catheter was connected to a cardiac output computer to measure the thermodilution cardiac output. Cardiac output measurements were obtained with the present method ($CO_{ICG}$) and the comparison thermodilution method ($CO_{TD}$) during baseline conditions, reduced flow conditions resulting from vagal stimulation, and increased flow conditions resulting from blood volume expansion with saline.

Results.

Average values of $CO_{ICG}$ and $CO_{TD}$ measured in baseline conditions in the 10 animals were 412 (±13) ml/min and 366 (±11) ml/min, respectively, in the expected range for anesthetized rabbits. In each animal, $CO_{ICG}$ was linearly related to $CO_{TD}$ as shown on the following Table 4. The slope of the regression line (range: 0.74-1.25) was not different from 1.0 in 8 studies. In the combined data from all 10 studies the linear relationship between $CO_{ICG}$ and $CO_{TD}$ had a slope (0.95±0.03) not different from 1.0 and an ordinate (77±10 ml/min) that was slightly >0.

TABLE 4

| Experiment | EQUATION | N | R |
|---|---|---|---|
| 1 | $CO_{ICG}$ = 094† (±0.08) $CO_{TD}$ + 84 (±23) | 21 | 0.94 |
| 2 | $CO_{ICG}$ = 1.25† (±0.17) $CO_{TD}$ − 0* (±39) | 17 | 0.88 |
| 3 | $CO_{ICG}$ = 0.74 (±0.11) $CO_{TD}$ + 122 (±26) | 20 | 0.85 |
| 4 | $CO_{ICG}$ = 0.90† (±0.05) $CO_{TD}$ + 98 (±15) | 11 | 0.99 |
| 5 | $CO_{ICG}$ = 1.08† (±0.11) $CO_{TD}$ + 84 (±47) | 14 | 0.94 |
| 6 | $CO_{ICG}$ = 1.07† (±0.09) $CO_{TD}$ + 16* (±33) | 14 | 0.96 |
| 7 | $CO_{ICG}$ = 1.15 (±0.06) $CO_{TD}$ + 29* (±25) | 12 | 0.99 |
| 8 | $CO_{ICG}$ = 0.82† (±0.09) $CO_{TD}$ + 83 (±37) | 12 | 0.94 |
| 9 | $CO_{ICG}$ = 0.88† (±0.12) $CO_{TD}$ + 98* (±62) | 16 | 0.89 |
| 10 | $CO_{ICG}$ = 1.05† (±0.08) $CO_{TD}$ − 20* (±33) | 15 | 0.97 |
| All | $CO_{ICG}$ = 0.95† (±0.03) $CO_{TD}$ + 74 (±10) | 152 | 0.94 |

These studies further established that cardiac output $CO_{ICG}$ measured with the present method is linearly related to thermodilution cardiac output $CO_{TD}$. The slope of the regression line between these variables was near 1.0 for most experiments, as well as for the grouped data from all experiments.

EXAMPLE 4

A. Noninvasive Calibration

One embodiment of the calibration system includes a method to determine non-invasively transcutaneously the concentration of a fluorescent indicator injected in the bloodstream by measuring the intensity of the fluorescence light emitted by the indicator when illuminated by a light source in or near the skin and the intensity of the light from that source reflected by or transmitted through the illuminated skin site.

In the pulse dye densitometer (Cardiac output and circulating blood volume analysis by pulse dye densitometry. Iijima T. et al. Journal of Clinical Monitoring, 13, 81-89, 1997, incorporated herein in its entirety by reference), light absorption is measured at two wavelengths: 805 nm where ICG absorption is near maximum and 890 nm where ICG absorption is very small. Assuming at first that tissue absorption of light is only due to blood hemoglobin and ICG, the ratio $C_{ICG}/C_{Hb}$ can be expressed as a function of the ratio $\psi$ of the optical densities measured at 805 nm and 890 nm, $$C_{ICG}/C_{Hb} = \frac{E_{Hb,805} - \Psi E_{Hb,890}}{\Psi E_{ICG,890} - E_{ICG,805}}$$

where E represents the absorption coefficient from Beer's Law. The latter is expressed as $I_x = I_0 e^{-E \cdot C \cdot x}$ with C=concentration, E=absorption coefficient, x=path length in substance. Note that if we assume that $E_{ICG,890}=0$, the ratio of the concentrations $C_{ICG}/C_{Hb}$ is linearly related to the ratio of the optical densities measured at two wavelengths.

Taking into account scattering and absorption by other material beside ICG and Hb, the developers of the pulse dye densitometer established that the ratio of the optical density changes between before and after ICG administration at 805 nm and 890 nm could be expressed as a function of the ratio $C_{ICG}/C_{Hb}$.

ICG fluorescence is proportional to the absorption of light by ICG at the wavelength of excitation (805 nm in the model above or 784 nm in our studies). Therefore, we hypothesized that the ratio $C_{ICG}/C_{Hb}$ can be derived from the ratio of the change in light signal measured at the wavelength of emission (related to ICG fluorescence) to the light signal measured at the wavelength of excitation (related to ICG and Hb absorption).

We considered a model of light propagation in tissue, which at first assumed that only hemoglobin and ICG were absorbers (See Table 5 below). The absorption coefficients of ICG and Hb were derived from the literature and considered to be independent of wavelength. We then added a dependence of the absorption coefficients on wavelength and tissue absorption in the model to investigate the effect of these factors.

We modeled transmission and fluorescence signals at 784 nm and 830 nm for different ICG concentrations and hemoglobin contents when absorption coefficients are the same, and the results are illustrated in the graphs of FIGS. 11A-11D. For this simple model, the transmitted excitation light decreases nonlinearly as a function of ICG concentration in the model and the curve varies with the hemoglobin content (see FIG. 11A). Also the emergent fluorescence light increases nonlinearly with ICG concentration (inner filter effect), and the curve varies with hemoglobin content (see FIG. 11B). Thus, the fluorescence signal varies markedly if there is more or less absorption by blood in the tissue.

However, the ratio (emergent fluorescence light/transmitted excitation light) is proportional to the ICG concentration and independent of the hemoglobin content of the tissue (see FIG. 11C). Therefore, by measuring the ratio and if the relationship is known, the ICG concentration can be estimated. Also, the ratio (emergent fluorescence light y/transmitted excitation light x) is proportional to the ratio (ICG concen-

TABLE 5

1-D model of light propagation and fluorescence generation

| Incident $I_0$ $F_0 = 0$ | $\Delta x$ Excitation absorbed Hb $I_0\mu_{a,Hb}C_{Hb}\Delta x$ Excitation absorbed ICG $I_0\mu_{a,ICG}C_{ICG}\Delta x$ Excitation absorbed total $I_0(\mu_{a,Hb}C_{Hb} + \mu_{a,ICG}C_{ICG})\Delta x$ Fluorescence produced ICG $Q \cdot I_0\mu_{a,ICG}C_{ICG}\Delta x$ Fluorescence absorbed Hb 0 Fluorescence absorbed ICG 0 Fluorescence absorbed total 0 | Excitation transmitted total $I_1 = I_0 - I_0(\mu_{a,Hb}C_{Hb} + \mu_{a,ICG}C_{ICG})\Delta x$ Fluo. transmitted total $F = Q \cdot I_0\mu_{a,ICG}C_{ICG}\Delta x$ | $\Delta x$ Excitation absorbed Hb $I_1\mu_{a,Hb}C_{Hb}\Delta x$ Excitation absorbed ICG $I_1\mu_{a,ICG}C_{ICG}\Delta x$ Excitation absorbed total $I_1(\mu_{a,Hb}C_{Hb} + \mu_{a,ICG}C_{ICG})\Delta x$ Fluorescence produced ICG $Q \cdot I_1\mu_{a,ICG}C_{ICG}\Delta x$ Fluorescence absorbed Hb $F_1\mu_{a,Hb}C_{Hb}\Delta x$ Fluorescence absorbed ICG $F_1\mu_{a,ICG}C_{ICG}\Delta x$ Fluorescence absorbed total $F_1(\mu_{a,Hb}C_{Hb} + \mu_{a,ICG}C_{ICG})\Delta x$ |
|---|---|---|---|
| | Excitation transmitted total $I_2 = I_1 - I_1(\mu_{a,Hb}C_{Hb} + \mu_{a,ICG}C_{ICG})\Delta x$ Fluo. transmitted total $F_2 = Q \cdot I_1\mu_{a,ICG}C_{ICG}\Delta x - F_1(\mu_{a,Hb}C_{Hb} + \mu_{a,ICG}C_{ICG})\Delta x$ | $\Delta x$ Excitation absorbed Hb $I_2\mu_{a,Hb}C_{Hb}\Delta x$ Excitation absorbed ICG $I_2\mu_{a,ICG}C_{ICG}\Delta x$ Excitation absorbed total $I_2(\mu_{a,Hb}C_{Hb} + \mu_{a,ICG}C_{ICG})\Delta x$ Fluorescence produced ICG $Q \cdot I_2\mu_{a,ICG}C_{ICG}\Delta x$ Fluorescence absorbed Hb $F_2\mu_{a,Hb}C_{Hb}\Delta x$ Fluorescence absorbed ICG $F_2\mu_{a,ICG}C_{ICG}\Delta x$ Fluorescence absorbed total $F_2(\mu_{a,Hb}C_{Hb} + \mu_{a,ICG}C_{ICG})\Delta x$ | ■ ■ ■ ■ ■ |

The following data and assumptions were applied to the model of Table 5:

$\mu_{a,ICG}=38.1$ $\mu l \cdot \mu g^{-1} \cdot mm^{-1}$ for wavelength $\lambda=784$ nm $\mu_{a,HbO2} \sim \mu_{a,Hb} = 0.0026$ $\mu l \cdot \mu g^{-1} \cdot mm^{-1}$ for wavelength $\lambda=784$ nm Initially, we assume that the absorption coefficients have the same values at 830 nm (fluorescence) and at 784 nm (incident excitation light).

$C_{Hb}=12-18$ $g \cdot dl^{-1}=120-180$ $\mu g/\mu l$ in blood $C_{ICG}$ max=0.005 $\mu g/\mu l$ in blood Tissue assumed to contain 10% blood Quantum yield of ICG fluorescence=0.04

Figure 11D:
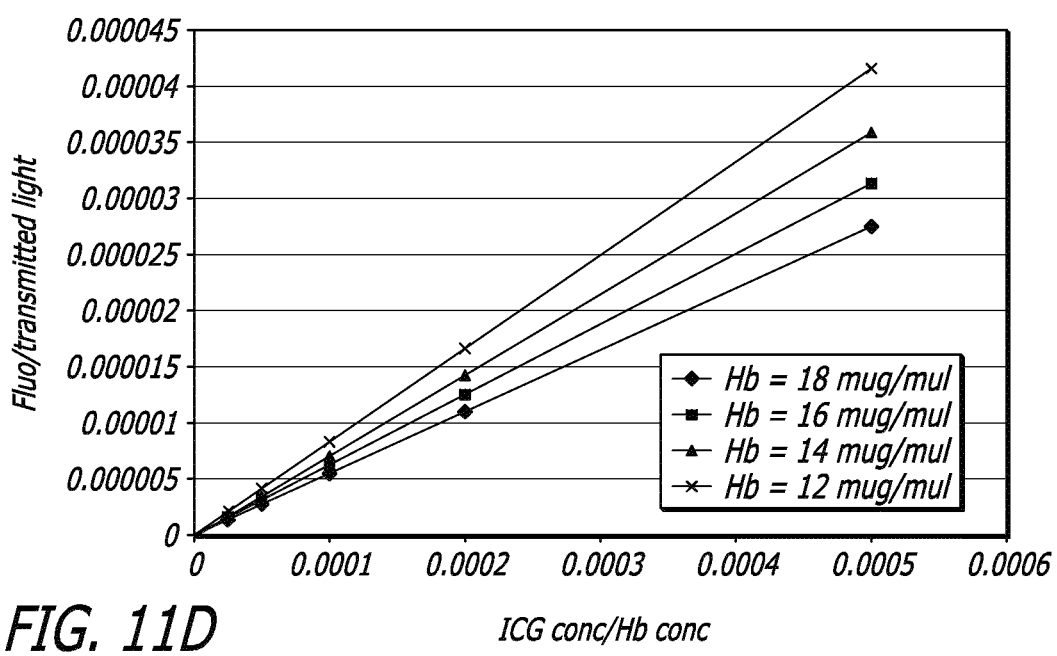

Transmission calculated through 40 mm tissue in 0.02 mm increment tration/Hb concentration) but in this case the slope varies with the hemoglobin content of the tissue (see FIG. 11D). In an alternative embodiment of the calibration system, the concentration of Hb may be obtained from a blood sample, and this concentration value can be used to determine the ratio of ICG value to Hb value, which can then be used with the ratio of transmitted excitation light to fluorescence light to determine the concentration of ICG for calibration.

We also modeled transmission and fluorescence signals and at 784 nm and 830 nm for different ICG concentrations and hemoglobin contents when absorption coefficients are the different and an additional absorber is included, and the results are illustrated in the graphs of FIGS. 12A-12D.

Absorption by ICG is actually slightly more elevated at 784 nm (excitation) than it is at 830 nm (fluorescence peak). In contrast oxy-hemoglobin absorption is less at 784 nm (excitation) than it is at 830 nm. In addition to blood hemoglobin and ICG, bloodless tissue absorbs to a certain extent. We determined various values from the literature:

$\mu_{a,ICG}$=38.1 µl·µg$^{-1}$·mm$^{-1}$ for wavelength λ=784 nm $\mu_{a,HbO2}$~$\mu_{a,Hb}$=0.0026 µl·µg$^{-1}$·mm$^{-1}$ for wavelength λ=784 nm $\mu_{a,ICG}$=34.1 µl·µg$^{-1}$·mm$^{-1}$ for wavelength λ=830 nm $\mu_{a,HbO2}$~$\mu_{a,Hb}$=0.0035 µl·µg$^{-1}$·mm$^{-1}$ for wavelength λ=830 nm $\mu_{a,tissue}$=0.1·mm$^{-1}$ independent of wavelength in the range 784-830 nm.

$C_{Hb}$=12–18 g·dl$^{-1}$=120–180 µg/µl in blood $C_{ICG}$ max=0.005 µg/µl in blood Tissue assumed to contain 10% blood Quantum yield of ICG fluorescence=0.04

Transmission calculated through 40 mm tissue in 0.02 mm increment

For this more complete model, the magnitude of the transmitted excitation light and emergent fluorescent lights are markedly decreased when compared to the first model primarily because of the absorption by bloodless tissue. Both signals follow the pattern found for the simple model. In particular, the emergent fluorescence light increases nonlinearly with ICG concentration (inner filter effect) and the curve varies with hemoglobin content.

Figure 12A:
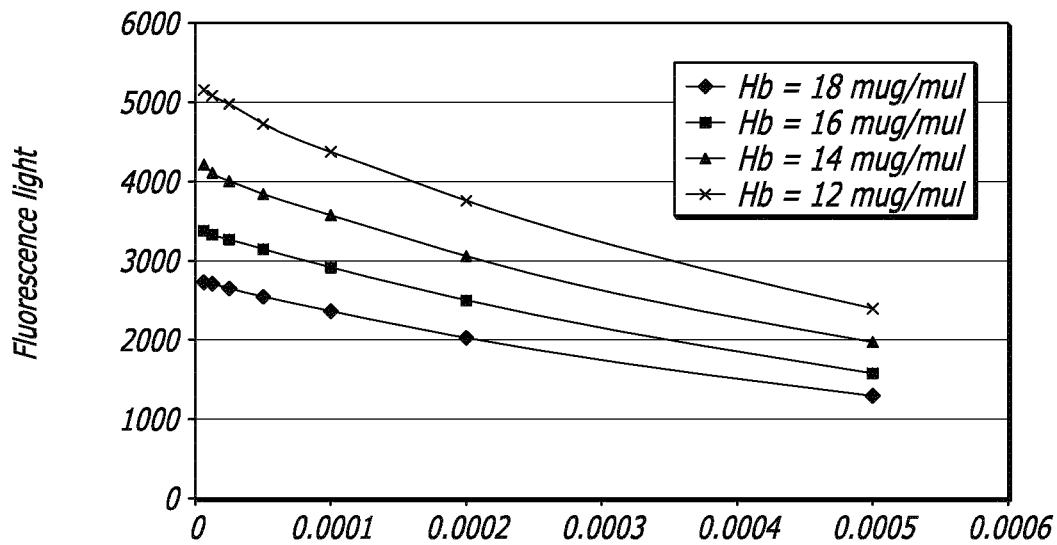
FIGS. 12A-12D are graphs showing transmission and fluorescence signals at 784 nm and 830 nm for different ICG concentrations and hemoglobin contents when absorption coefficients vary with wavelength and an additional absorber is included.
Figure 12B:
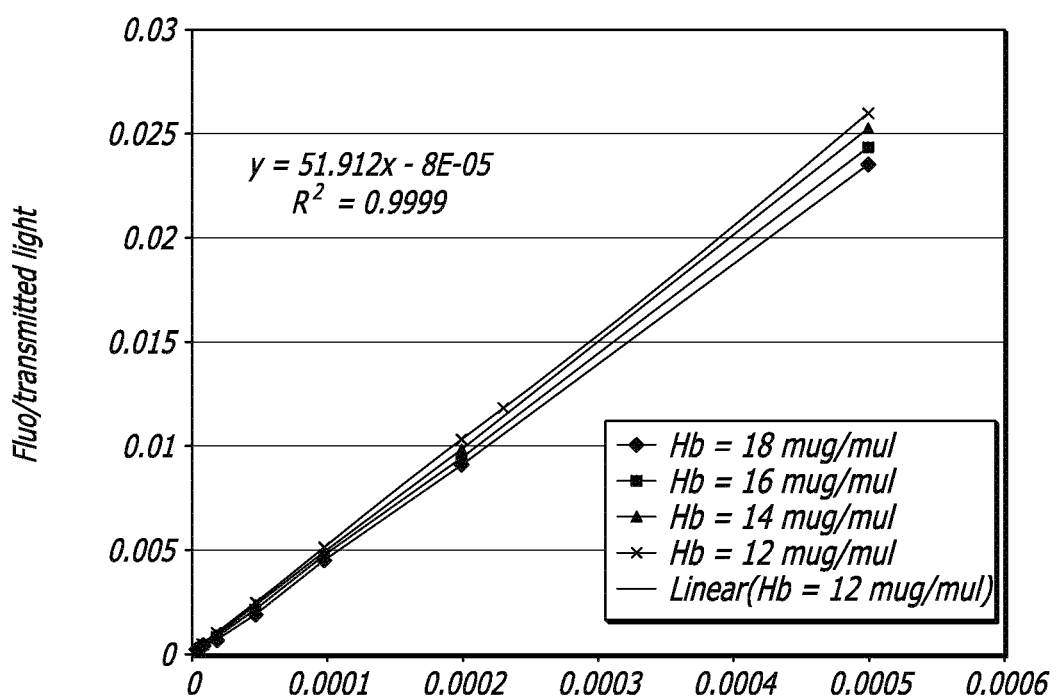
Figure 12C:
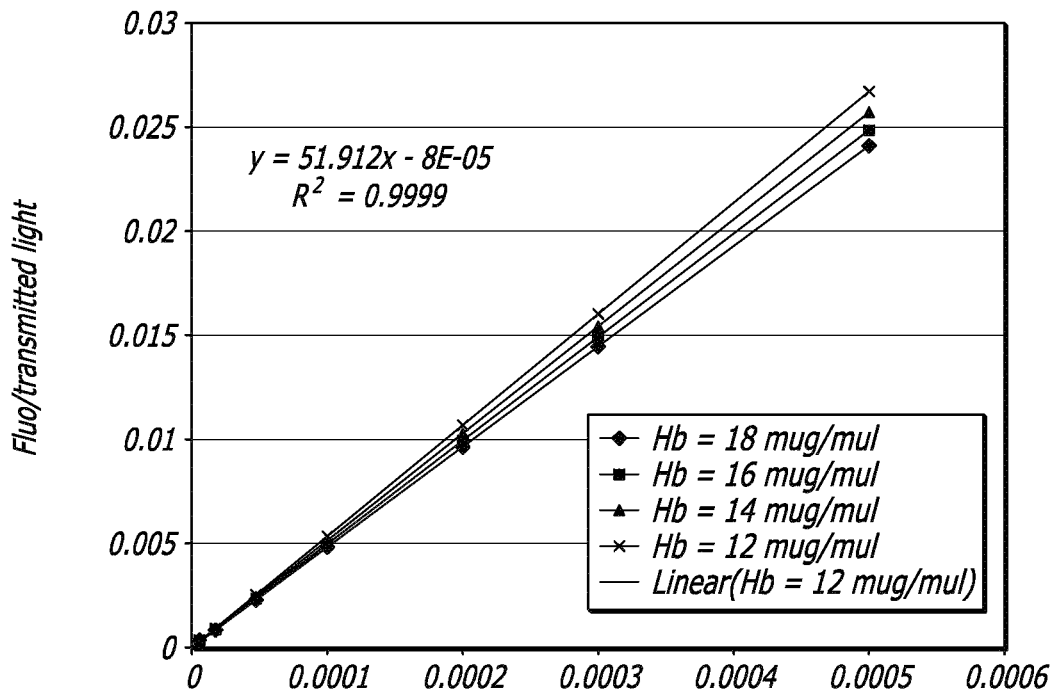
Figure 12D:
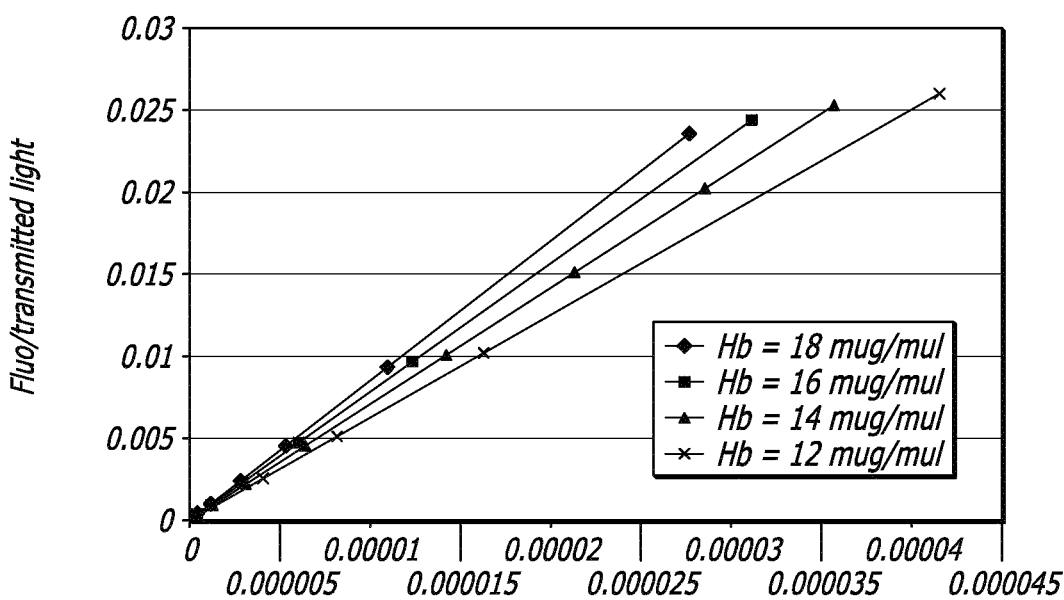

As before the ratio (emergent fluorescence light/transmitted excitation light) is proportional to the ICG concentration (See FIG. 12C). While the slope is dependent on the hemoglobin content, there are only small differences between the four levels of hemoglobin considered. This suggests that by measuring the ratio of the fluorescence/transmitted light, the ICG concentration can be estimated once the linear relationship is determined and possibly including a factor that accounts for the hemoglobin content.

While these models do not consider tissue scattering, the latter is often assumed to increase the pathlength of light in tissue by a fixed proportionality factor: the pathlength factor (about 3.6 for human forearm, see Measurement of hemoglobin flow and blood flow by near-infrared spectroscopy. Edwards A. D. et al., *J. Appl. Physiol.* 75, 1884-1889, 1993, the entire contents of which are incorporated herein by reference). This suggests that the model analysis above would likely remain valid even in the presence of scattering.

Other biocompatible fluorescent dyes such as fluorescein and rhodamine would also be suitable in the noninvasive calibration of the example 4 above. Fluorescein in blood plasma has a peak fluorescence of about 518±10 nm with an optimal excitation wavelength of about 488 nm (Hollins, supra; Dorshow, supra). Rhodamine in blood plasma has a peak fluorescence of about 640±10 nm with an optimal excitation wavelength of about 510 nm.

The previous description of the disclosed embodiments is provided to enable any person skilled in the art to make or use the cardiac output monitor devices, methods and systems. Various modifications to these embodiments will be readily apparent to those skilled in the art, and the generic principles defined herein may be applied to other embodiments without departing from the spirit or scope of the devices, methods and systems described herein. Thus, the cardiac output devices, methods and systems are not intended to be limited to the embodiments shown herein but are to be accorded the widest scope consistent with the principles and novel features disclosed herein.

The invention claimed is:

1. A cardiac output system for repetitive cardiac output measuring of a freely moving individual comprising:
    a) a dye calibration and delivery system (CDS) configured to be worn by the individual comprising:
        i. a calibration station configured to hold at least one calibration cartridge and to draw blood from the individual; and
        ii. a dye delivery station configured to hold at least one dye delivery cartridge and to administer a predetermined amount of dye to the individual's blood stream;
    b) a sensing device configured to be worn by the individual comprising:
        i. at least one illumination source configured to rest against the individual's skin and to excite the administered dye in the blood stream; and
    c) at least one photodetector configured to rest against the individual's skin and to detect fluorescence intensity reflected from or transmitted by the illuminated dye; and
    d) an external device configured to wirelessly communicate with at least the CDS and the sensing device, and to determine the cardiac output of the individual based on the detected fluorescence intensity and the information indicative of the concentration of the dye in the blood that was drawn from the individual.

2. The system of claim 1 further comprises hardware and software configured to operate the system and the CDS, the sensing device, and the at least one photodetector.

3. The system of claim 1, wherein the system further includes a dye mixing station configured to hold the calibration and/or dye delivery cartridges.

4. The system of claim 3, wherein the cartridges are configured to contain a plurality of separately sealed chambers having different contents.

5. The system of claim 4, wherein the contents include any one of dye, sterile water or sterile saline.

6. The system of claim 5, wherein the mixing station is configured to automatically mix the contents of the cartridges by an ultrasonic process.

7. The system of claim 3, wherein the cartridges are configured to be of a transparent material.

8. The system of claim 1, wherein the calibration station includes at least one element that is configured to illuminate the calibration cartridge having a dye concentration and sense the fluorescence intensity transmitted from or reflected by the dye.

9. The system of claim 8, wherein the external device is configured to calibrate the system based on the sensed fluorescence intensity.

10. The system of claim 1, wherein the external device is configured to enable the CDS remotely to administer the dye to the individual.

11. The system of claim 10, wherein the CDS is configured to administer the dye at predetermined times.

12. The system of claim 11, wherein the dye is administered repetitively based on the individual's measured heart rate.

13. The system of claim 12, wherein the dye is administered while the individual is on an exercise equipment.

14. The system of claim 10, wherein the CDS is configured to administer a predetermined amount of dye to the individual based on the individual's weight.

15. The system of claim 1, wherein the dye is indocyanine green (ICG).

16. The system of claim 1, wherein the CDS is configured to draw blood and/or administer dye to the individual through plurality of onboard attached IV lines.

17. The system of claim 1, wherein the sensing device is configured to detect fluorescence intensity reflected from or transmitted by the administered dye for a predetermined duration.

18. The system of claim 1, wherein the calibration station is further configured to retain at least one final calibration cartridge.

19. The system of claim 18, wherein the CDS is configured to draw a final blood sample from the individual into the final calibration cartridge.

20. The system of claim 19, wherein the external device is configured to determine the concentration of the dye in the blood sample of the final calibration cartridge.

21. The system of claim 20, wherein the external device configured to determine the blood volume within the individual's cardiovascular system based on the concentration of the dye in the blood sample.

22. The system of claim 19, wherein the CDS is configured to draw a final blood sample at the end of a repetitive cardiac output measuring process.

23. The system of claim 1, wherein the external device is configured to communicate with the CDS and the sensing device through a dongle.

24. The system of claim 23, wherein the external device is any one of PDA, laptop or desktop computer.

* * * * *